United States Patent [19]

Oppenheim et al.

[11] Patent Number: 5,059,529
[45] Date of Patent: Oct. 22, 1991

[54] STABILIZED EXPRESSION VECTORS CONTAINING $\lambda P_L$ PROMOTER AND THE GENE FOR THE $CI_{434}$ REPRESSOR, PLASMIDS CONTAINING THE VECTORS, HOSTS CONTAINING THE PLASMIDS AND RELATED METHODS

[75] Inventors: Amos B. Oppenheim; Giladi Locker, both of Jerusalem, Israel

[73] Assignee: Bio-Technology General Corp., New York, N.Y.

[21] Appl. No.: 317,629

[22] Filed: Mar. 1, 1989

Related U.S. Application Data

[63] Continuation of Ser. No. 644,551, Aug. 27, 1984, abandoned.

[51] Int. Cl.$^5$ .................. C12N 15/18; C12N 15/63; C12N 15/70; C12N 15/73
[52] U.S. Cl. .................. 435/69.4; 435/320.1; 435/252.33; 935/38; 935/29; 935/60; 935/72
[58] Field of Search .................. 435/69.1, 320, 252.33, 435/320.1, 69.4; 935/29, 38, 60, 73

[56] References Cited

U.S. PATENT DOCUMENTS

| | | | |
|---|---|---|---|
| 4,436,815 | 3/1984 | Hershberger et al. | 435/172 |
| 4,578,355 | 3/1986 | Rosenberg | 435/317 |
| 4,650,761 | 3/1987 | Hershberger et al. | 435/172.3 |

FOREIGN PATENT DOCUMENTS

| | | |
|---|---|---|
| 0041767 | 12/1981 | European Pat. Off. |
| 0049619 | 4/1982 | European Pat. Off. |

OTHER PUBLICATIONS

Brosius et al., 1981, J. Mol. Biol., 148:107–127.
Seeburg et al., 1983, DNA, 2, #1, pp. 37–45.
Bernard, H. V. et al., Gene 5: 59 (1979).
Derom, C. et al., Gene 17: 45 (1982).
Gheysen, D. et al., Gene 17: 55 (1982).
Hedgpeth, J. et al., Mol. Gen. Genet. 163: 197 (1978).
Derynck, R. et al., Nature 287: 193 (1980).
Oppenheim, A. B. et al., J. Mol. Biol. 158: 327 (1982).
Shimatake, H. et al., Nature 292: 128 (1981).
Courtney, M. et al., Proc. Natl. Acad. Sci. (U.S.A.) 81: 669–673 (1984).
Lautenberger, J. A. et al., Gene 23: 75–84 (1983).
Lautenberger, J. A. et al., Science 221: 858–860 (1983).
Shatzman, A. R. et al., 14 Miami Winter Symposium, abstract, p. 98 (1982).
Amann, E. et al., Gene 25: 167 (1983).
Zabeau, M. et al., The EMBO Journal 10: 1217 (1982).

*Primary Examiner*—Richard A. Schwartz
*Assistant Examiner*—S. L. Nolan
*Attorney, Agent, or Firm*—John P. White

[57] ABSTRACT

An improved vector upon introduction into a suitable host containing the thermolabile repressor $C_I$ renders the host capable of effecting expression of a desired gene. The vector is a double-stranded DNA molecule which includes in 5' to 3' order the following: the promoter and operator $P_LO_L$ from lambda bacteriophage; the N utilization site; a first restriction enzyme site permitting replacement of the ribosomal binding site which follows thereafter; a ribosomal binding site; an ATG initiation codon or DNA which is converted into an ATG initiation codon upon insertion of the desired gene into the vector; a second restriction enzyme site for inserting the gene in phase with the ATG codon; a $T_1T_2$ rRNA transcription termination sequence; an origin of replication; and a fragment designated $cI^{434}$ on which is included the gene for the repressor protein and its associated promoter and operator. Additionally, the vector may include a gene associated with a selectable or identifiable phenotypic trait which is manifested when the vector is present in the host. The distance between the 3' end of $P_LO_L$ and the 5' end of the N utilization site is less than about 80 base pairs. The distance between the 3' end of the N utilization site and the 5' end of the ribosomal binding site is less than about 300 base pairs.

Plasmids have been constructed from the vectors and used to produce bovine growth hormones.

4 Claims, 24 Drawing Sheets

1. Partial NdeI
2. Fill in
3. Ligase

STABILIZED EXPRESSION VECTORS CONTAINING λP$_L$ PROMOTER AND THE GENE FOR THE CL$_{434}$ REPRESSOR, PLASMIDS CONTAINING THE VECTORS, HOSTS CONTAINING THE PLASMIDS AND RELATED METHODS

This application is a continuation of U.S. Ser. No. 644,551, filed Aug. 27, 1984, now abandoned, the contents of which are hereby incorporated by reference.

BACKGROUND OF THE INVENTION

One aspect of genetic engineering involves the insertion of foreign DNA sequences derived from eucaryotic sources into *Escherichia coli* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby effect the relative efficiency of the promoter. The efficiency depends on the affinity of the RNA polymerase for the promoter.

The efficiency of translation is affected by the stability of the mRNA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the structure of the mRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attempts to produce high amounts of eucaryotic polypeptides in bacterial cells involves the inability of cells producing large amounts of mRNA to grow efficiently. This difficulty can be eliminated by preventing transcription by a process known as repression. In repression genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor.

Numerous reports may be found in the literature concerning the cloning of eucaryotic genes in plasmids containing the P$_L$ promoter from λ bacteriophage. (Bernard, H.V., et al., Gene (1979) 5, 59; Derom, C., et al., Gene (1982) 17, 45; Gheysen, D., et al., Gene (1982) 17, 55; Hedgpeth, J., et al., Mol. Gen. Genet. (1978) 163, 197; Remaut, E., et al., (1981) Gene 15, 81 and Derynck, R., et al., Nature (1980) 287, 193. In addition, European patent application No. 041,767, published Dec. 16, 1981, describes expression vectors containing the P$_L$ promoter from λ bacteriophage. However, none of these references describe the use of the C$_{II}$ ribosomal binding site.

The use of a vector containing the P$_L$ promoter from λ bacteriophage and the CII ribosomal binding site has been described. (Oppenheim, A.B., et al., J. Mol. Biol. (1982) 158, 327 and Shimatake, H. and Rosenberg, M., Nature (1981) 292, 128.) These publications describe the production of increased levels of C$_{II}$ protein but do not involve or describe the production of eucaryotic proteins.

Other vectors which contain the P$_L$ promoter and the cII ribosomal binding site have also been described (Courntey, M., et al., PNAS (1984) 81, 669-673; Launtenberger, J.A., et al., Gene (1983) 23, 75-84 and Lautenberger, J.A., et al., Science (1983) 221, 858-860). However, all of these vectors lead to the production of fused proteins which contain the amino terminal portion of the C$_{II}$ protein.

In 1982 Shatzman and Rosenberg presented a poster at the 14th Miami Winter Symposium (Shatzman, A.R. and Rosenberg, M., 14 Miami Winter Symposium, abstract p98 [1982]). This abstract provides a non-enabling disclosure of the use of a vector containing P$_L$ from λ bacteriophage, Nut and the C$_{II}$ ribosomal binding site to synthesize a "eucaryotic" polypeptide (SV40 small T antigen is not a polypeptide of eucaryotic origin but is a protein of viral origin produced in eucaryotic cells) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed.

Applicants are aware of the existence of a pending U.S. patent application in the name of M. Rosenberg filed under Ser. No 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a λ mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the C$_{II}$ ribosomal binding region has been altered (p3, line 27).

Pending co-assigned U.S. patent application Ser. No. 514,188, filed July 15, 1983, describes novel vectors useful for the expression of polypeptides in bacteria. These vectors include $P_LO_L$, N utilization site for binding antiterminator N protein, ribosomal binding site, ATG codon, restriction enzyme site for inserting the gene encoding the desired polypeptide, an origin of replication and a selectable marker. In these vectors the distance between the N utilization site and the ribosomal binding site is greater than about 300 base pairs. In addition, each of these vectors contains a specific ribosomal binding site which cannot be readily replaced. These vectors are not equally useful for expression of different polypeptides.

$T_1T_2$ rRNA transcription termination sequences have been described. (Brosius, J., et al., J. Mol. Biol. (1981) 148, 107). The placement of T1T2 rRNA termination sequences at the 3' end of a procaryotic gene and the expression of such gene under the control of a promoter have been described. (Amann, E. et al., Gene (1983) 25, 167; Zabeau, M., et al., The EMBO Journal (1982) 1, 1217 ).

European patent application No. 81304573.9, published Apr. 14, 1982 under European publication No. 049,619, discloses the use of the λcI857 thermoinducible repressor as a stabilizing element. The repressor is cloned on the plasmid. A λcI90 prophage defective in repressor synthesis is introduced by infection. The prophage is maintained by the cloned repressor at temperatures below 32° C. Any cell losing the plasmid will be lysed. If the temperature is increased to above 38° C. the repressor is destroyed or inactivated and the cells lyse. This stabilization system is not compatible with the vectors of this invention which include $\lambda P_L$ promoter and which express polypeptides at temperatures above 38° C.

The present invention relates to expression vectors which unexpectedly provide enhanced expression of different polypeptides. By employing different ribosomal binding sites in the vectors of this invention it is possible to achieve enhanced expression levels of different polypeptides relative to the levels achieved with the previous vectors. In addition, using the same ribosomal binding sites as in the previous vectors, it is possible to achieve enhanced expression of the same polypeptides. Moreover, by placing $T_1T_2$ rRNA transcription termination sequences at the 3' end of the gene encoding a polypeptide whose expression is desired, it is possible to increase the amount of a desired polypeptide relative to the total polypeptide produced by a bacterial host. Further, the vectors of this invention are stably present in the host bacteria and prevent loss during bacterial growth of plasmids which include the vectors and genes encoding desired polypeptides. In this way, yield reduction caused by plasmid instability is overcome. Finally, use of these vectors avoids the use of antibiotic resistance as a selectable marker permitting lower costs for producing polypeptides.

SUMMARY OF THE INVENTION

This invention concerns an improved expression vector which upon introduction into a suitable bacterial host cell, e.g., Escherichia coli, containing the thermolabile repressor $C_I$ renders the host cell capable, upon increasing the temperature of the host cell to a temperature at which the repressor is inactivated, of effecting expression of a desired gene inserted into the vector and production of the polypeptide encoded by the gene comprising:

a double-stranded DNA molecule which includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA sequence which contains a $T_1T_2$ rRNA sequence;

and which additionally includes a DNA sequence which contains an origin of replication from a bacterial plasmid capable of autonomous replication in the host cell and a DNA sequence which contains the fragment designated cI$^{434}$, such fragment including the gene for the cI$^{434}$ repressor protein and its associated promoter and operator, the distance between the 3' end of the $P_LO_L$ promoter and operator sequence and the 5' end of the N utilization site being less than about 80 base pairs and the distance between the 3' end of the N utilization site and the 5' end of the ribosomal binding site being less than about 300 base pairs. Desirably, the $T_1T_2$ rRNA termination sequence is less than about 100 base pairs from the 3' end of the second restriction enzyme site, more desirably it is less than about 20 base pairs from the 3' end of the site. Desirably, the cI$^{434}$ fragment is located after the 3' end of the $T_1T_2$ rRNA termination sequence. Additionally, the vector may include a selectable or identifiable marker. The presently preferred vector is p579 into the ClaI site of which the cI$^{434}$ fragment has been inserted.

Genes, e.g., cDNAs, encoding desired polypeptides, such as growth hormones, e.g., bovine, porcine, chicken or human growth hormones, human superoxide dismutase, human apolipoprotein E or analogs thereof, may be inserted into the second restriction enzyme site of the vector to create plasmids. The plasmids in turn can be introduced into suitable hosts where the genes can be expressed and the desired polypeptide produced. The presently preferred plasmid for bGH is pHG50. Preferred hosts include Escherichia coli lacking the cI$^{434}$ repressor protein, e.g., A1645 (λi434cI-- miniTn10).

The resulting host vector systems can be employed to manufacture polypeptides, e.g. growth hormones. Host cells containing the plasmids are grown under suitable conditions permitting production of polypeptide and the resulting polypeptide is recovered.

DESCRIPTION OF THE FIGURES

The restriction maps for each of the plasmids shown in FIGS. 1-24 do not identify all restriction sites present on each plasmid. In some cases restriction sites are shown in one figure but not in another. However, in all cases those restriction sites necessary for a complete understanding of the invention are shown.

A plasmid containing bGH cDNA, D4 (ATCC No. 31826), was digested with HaeII. The resulting 1600 base pair large fragment was purified and digested at 37° C. for 5 minutes with S1 exonuclease. A synthetic EcoRI linker with the sequence:

GGAATTCC

CCTTAAGG was attached to the ends of the resulting fragments by ligation. The ligation mixture was cleaved with EcoRI and inserted into pBR322 (ATCC No. 37017) which had been cleaved with EcoRI. A clone, pALRI, was obtained which upon cleavage with EcoRI released a 1200 base pair fragment with the sequence:

AATTCCCAGCCATG...
    GGGTCGGTAC...

at the 5' end. This sequence demonstrates that pALRI contains an EcoRI restriction site which includes the TTC codon for residue number 1 (phenylalanine) of natural bGH. pALRI was subjected to a partial cleavage with PstI. The digest was treated with DNA polymerase I large fragment (Klenow) and HindIII linkers with the sequence:

GAAGCTTC

CTTCGAAG were attached by ligation. The ligation mixture was cleaved with EcoRI and HindIII. The fragment containing bGH cDNA was isolated and subcloned into pBR322 between the EcoRI and HindIII restriction sites to give pAL500 (ATCC No. 39782).

Figure 1:
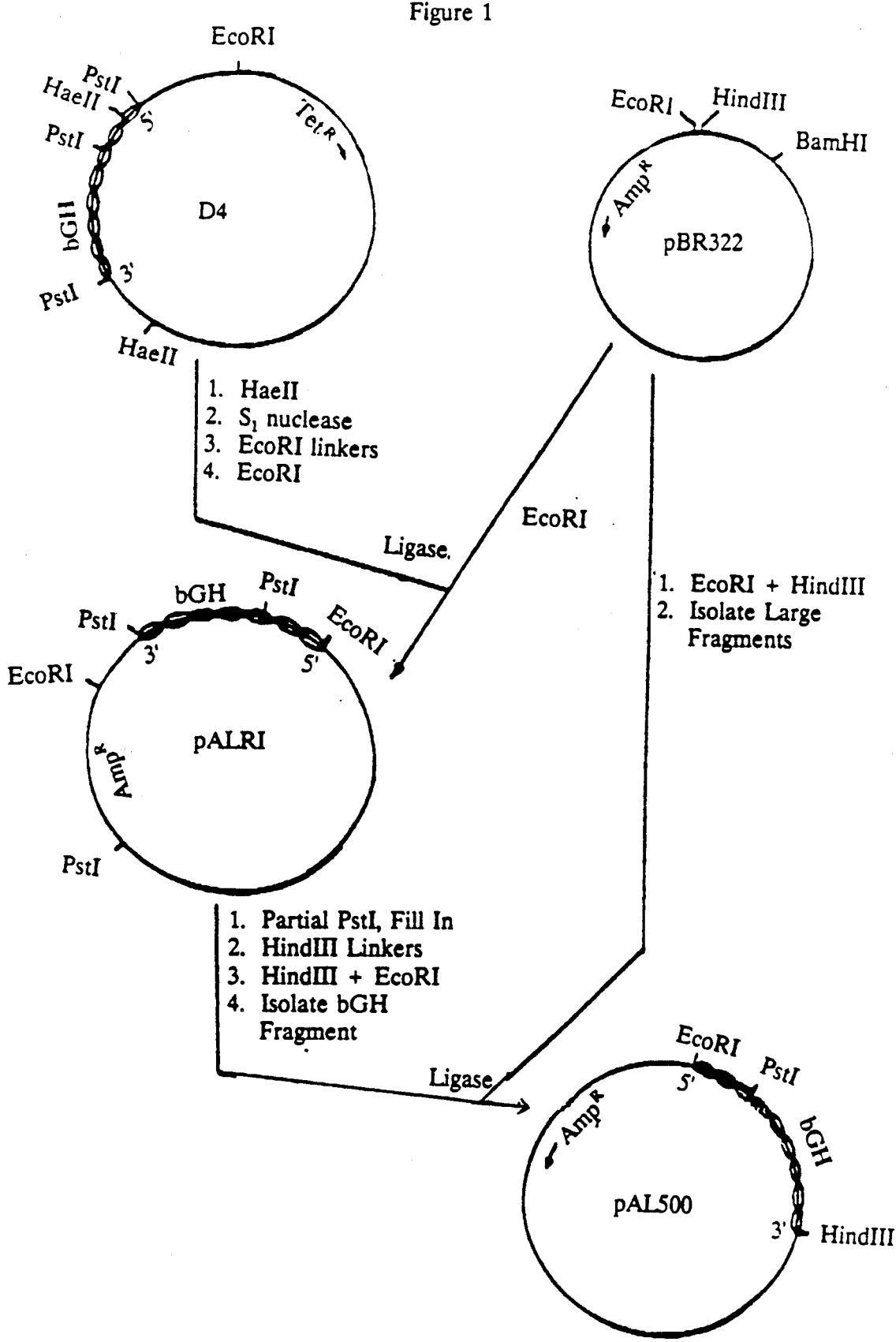
FIG. 1. Construction of pAL500.
Figure 2:
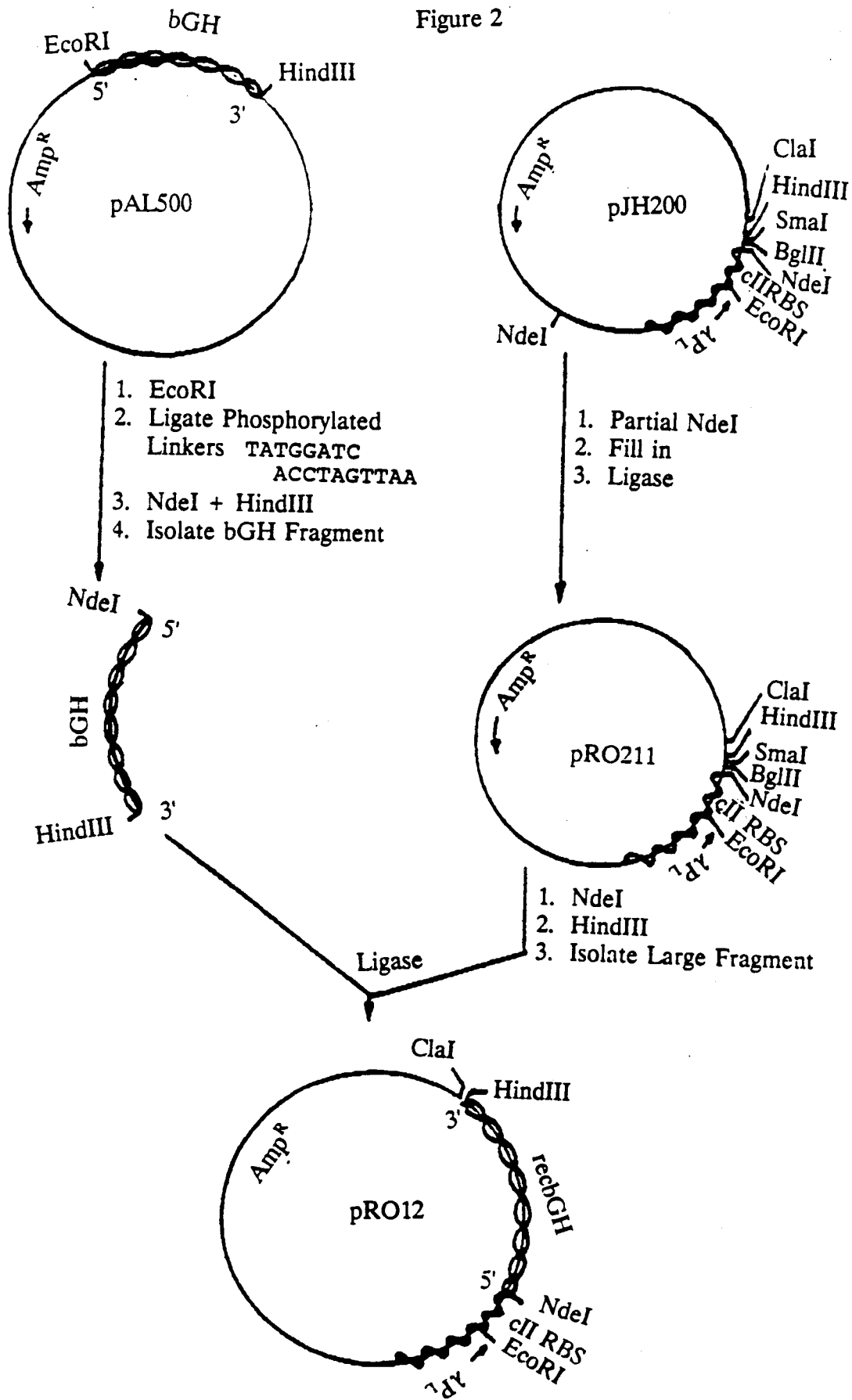

FIG. 2. Construction of pRO211 and pRO12.

The plasmid pJH200 (ATCC No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bGH fragment isolated from pAL500 (ATCC No. 39782) to give pRO12. (The NdeI-HindIII fragment was produced from pAL500 by digesting it with EcoRI and ligating to the ends of the digestion product synthetic linkers with the sequence:

TATGGATC
ACCTAGTTAA

The ligation mixture was digested with NdeI and HindIII and the resulting NdeI-HindIII bGH fragment isolated.)

Figure 3:
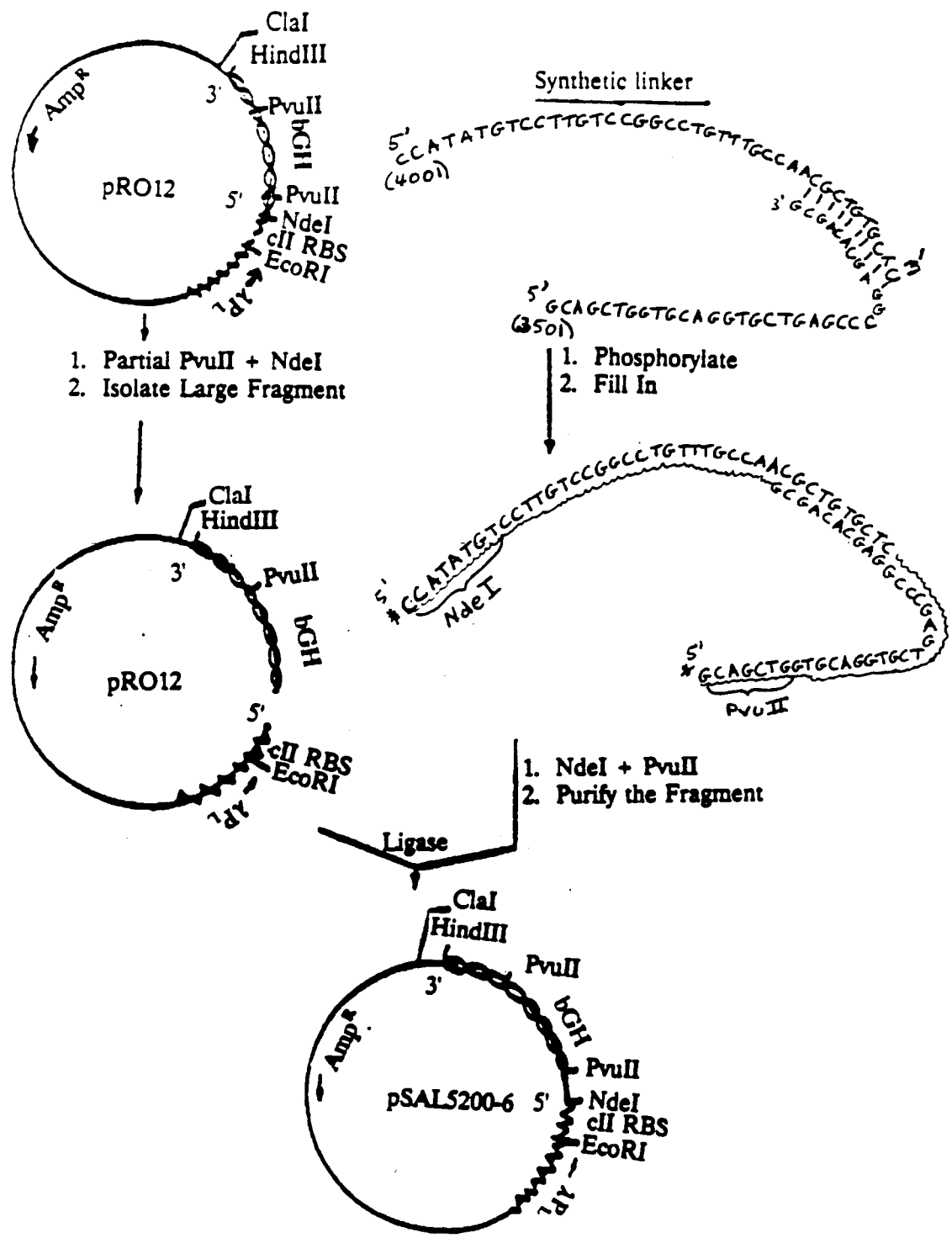

FIG. 3. Construction of pSAL 5200-6 pRO12 (FIG. 2) was partially digested with PvuII followed by digestion with NdeI to eliminate a 72 base pair fragment. A synthetic DNA fragment coding for the first 24 amino acids of the N-terminus of authentic bGH was ligated to the digested pRO12.

The synthetic DNA fragment was constructed by annealing two phosphorylated synthetic single-stranded DNAs of the sequence:

CCATATGTCCTTGTCCGGCCTGTTTGCCAACGCTGTGCTC-3'
3'-GCGACACGAGGCCCGAGTCGTGGACGTGGTCGACG

The annealed fragment was treated with DNA polymerase I (Klenow) in the presence of all four deoxyribonucleoside triphosphates in order to form the full length double-stranded DNA. The fragment was digested with PvuII and NdeI before ligation to pRO12 to form pSAL 5200-6.

Figure 4:
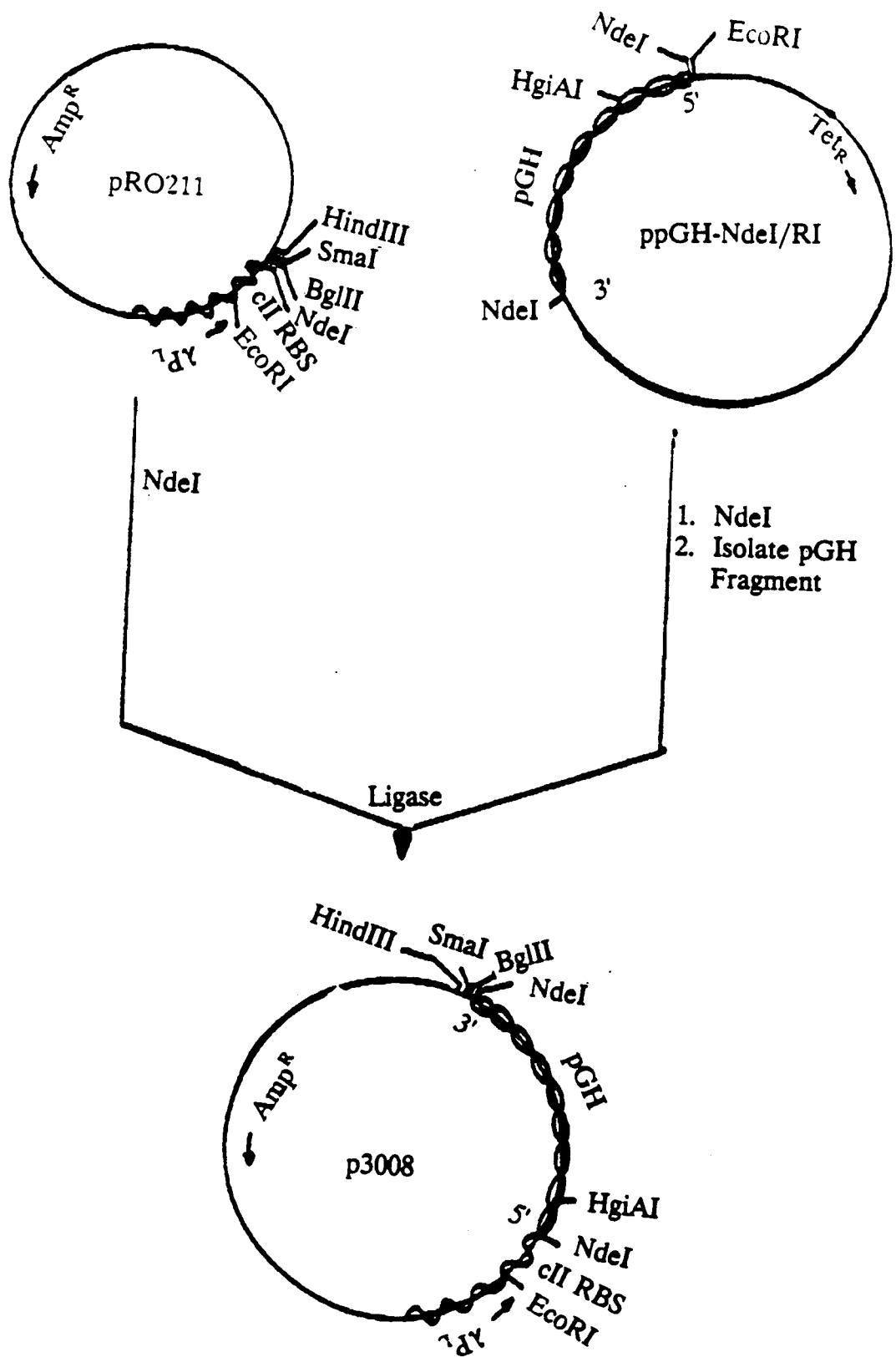

FIG. 4. Construction of p3008.

p3008 (ATCC No. 39804) was constructed by ligating NdeI-digested pRO211 (FIG. 2) with the pGH fragment isolated from an NdeI digest of the plasmid ppGH-NdeI/RI.

ppGH-NdeI/RI contains full length pGH cDNA to both ends of which NdeI sites have been added by means of synthetic linkers.

Figure 5:
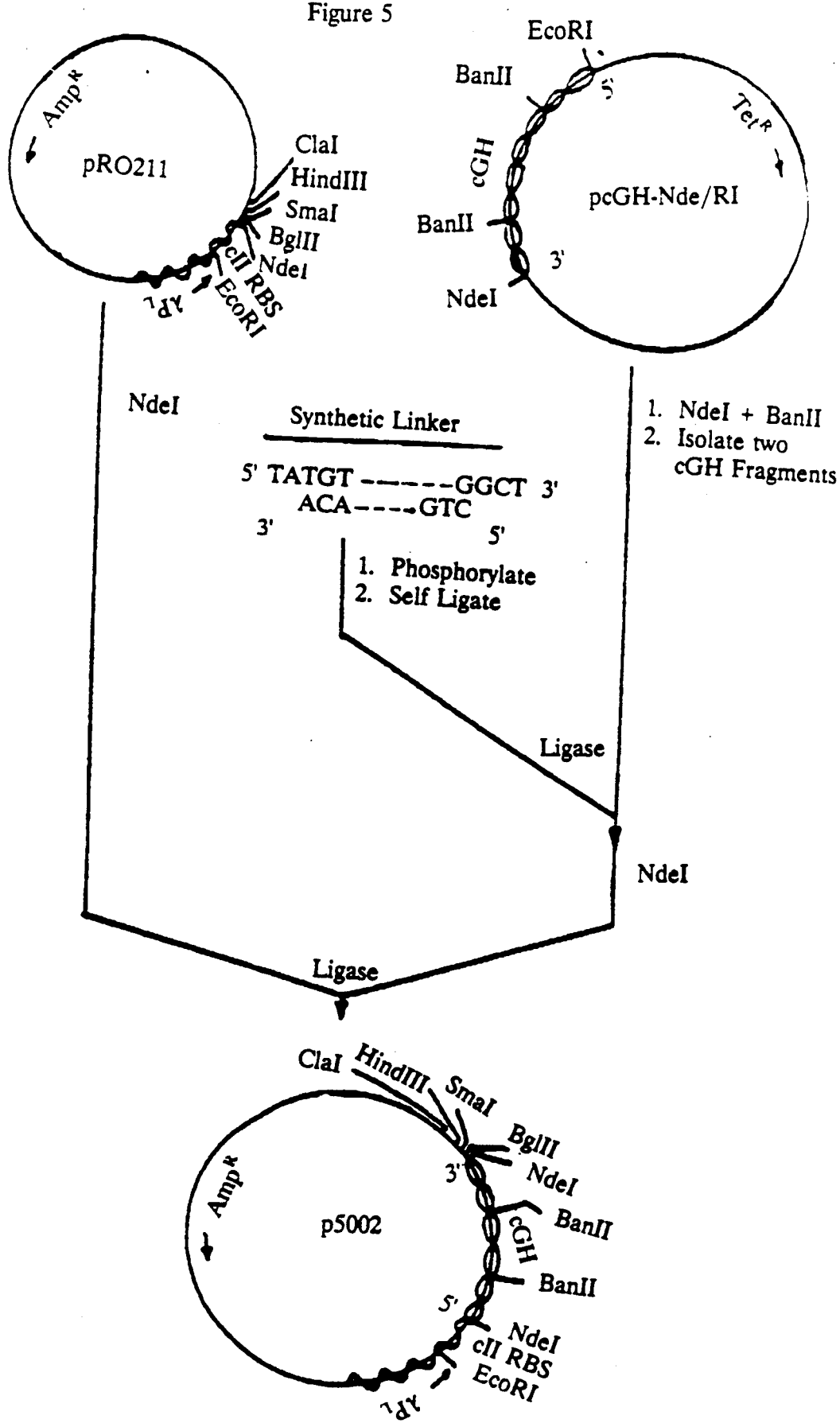

FIG. 5. Construction of p5002.

p5002 was constructed by tripartite ligation of a dimerized synthetic linker and the 2 cGH fragments isolated from an NdeI and BanII digest of the plasmid pcGH-NdeI/RI. The ligation mixture was digested with NdeI and then ligated to the expression vector pRO211 (FIG. 2) after it had been restricted with NdeI. A colony containing the plasmid p5002 was isolated.

The synthetic linker was constructed from two single-stranded synthetic DNAs of the sequence:

TATGTTCCCTGCCATGCCCCTCTCCAACCTGTTTGCCAACGCTGTGCTGAGGGCT
 ACAAGGGACGGTACGGGGAGAGGTTGGACAAACGGTTGCGACACGACTC

The linker was phosphorylated before ligation. The linker codes for the first 18 amino acids of the N-terminus of the authentic cGH.

The plasmid pcGH-NdeI/RI contains full length cGH cDNA at the 5' end of which there is an EcoRI restriction site and at the 3' end of which there is an NdeI restriction site. These restriction sites were added by means of synthetic linkers.

Figure 6:
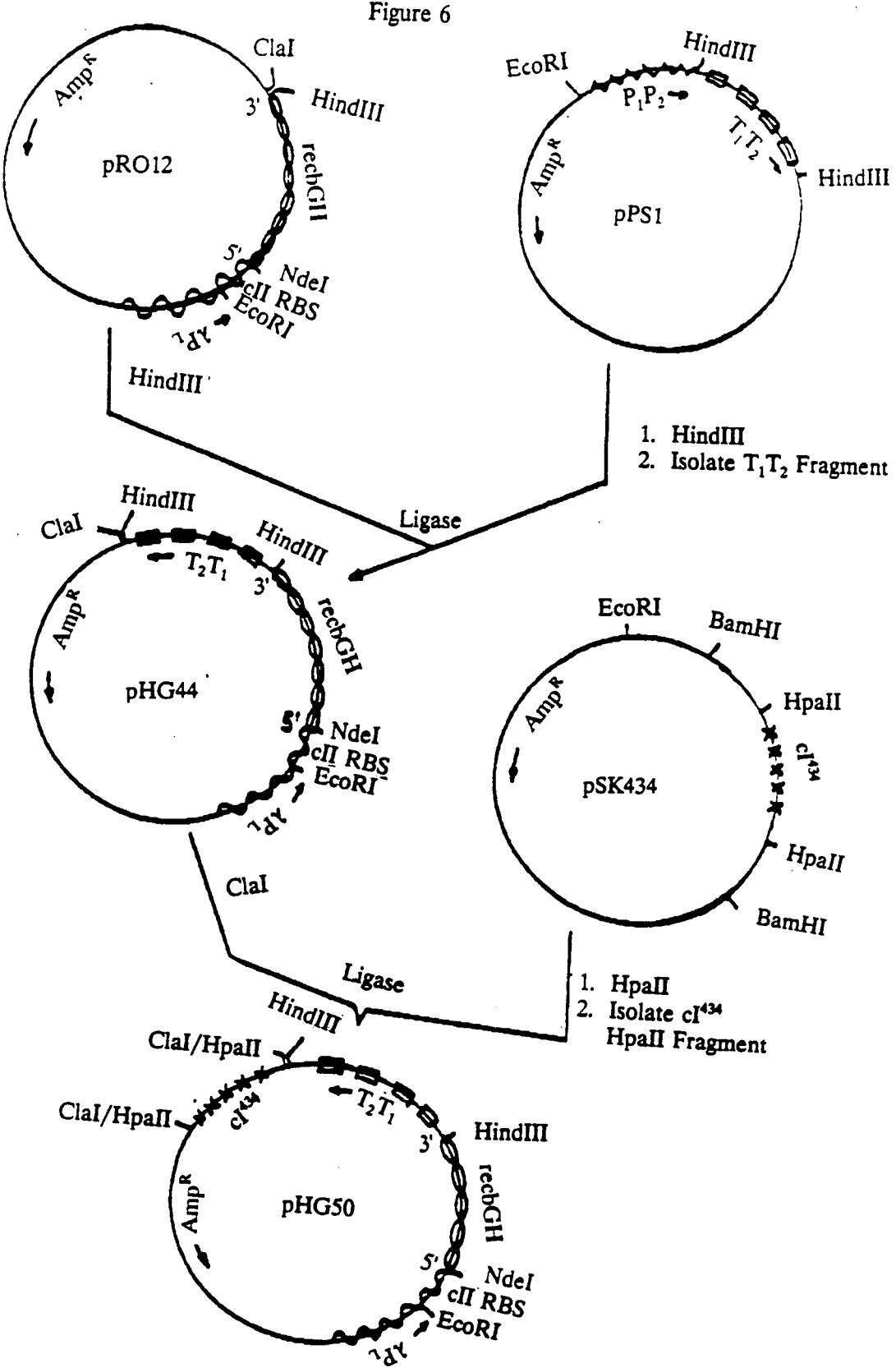

FIG. 6. Construction of pHG44 and pHG50.

pRO12 (FIG. 2) was digested with HindIII. The linear form DNA (form III) was purified from agarose gel and ligated to a HindIII-HindIII fragment of about 1200 base pairs which contains the rRNA opcron transcription termination sequences $T_1T_2$. The $T_1T_2$ HindIII-HindIII fragment was isolated from plasmid pPS1 (ATCC No. 39807) which had been digested with HindIII. The resulting plasmid pHG44 (ATCC No. 39806) contains the $T_1T_2$ sequences at the 3' end of the recombinant (rec) bGH sequence.

The plasmid pSK434 (ATCC No. 39784) containing the $\lambda cI^{434}$ repressor sequences was digested with HpaII. The $\lambda cI^{434}$ HpaII-HpaII fragment was isolated and ligated to pHG44 which had been digested with ClaI. The resulting plasmid pHG50 (ATCC No. 39805) contains the $T_1T_2$ transcription termination sequences and the $\lambda cI^{434}$ repressor sequence.

Figure 7:
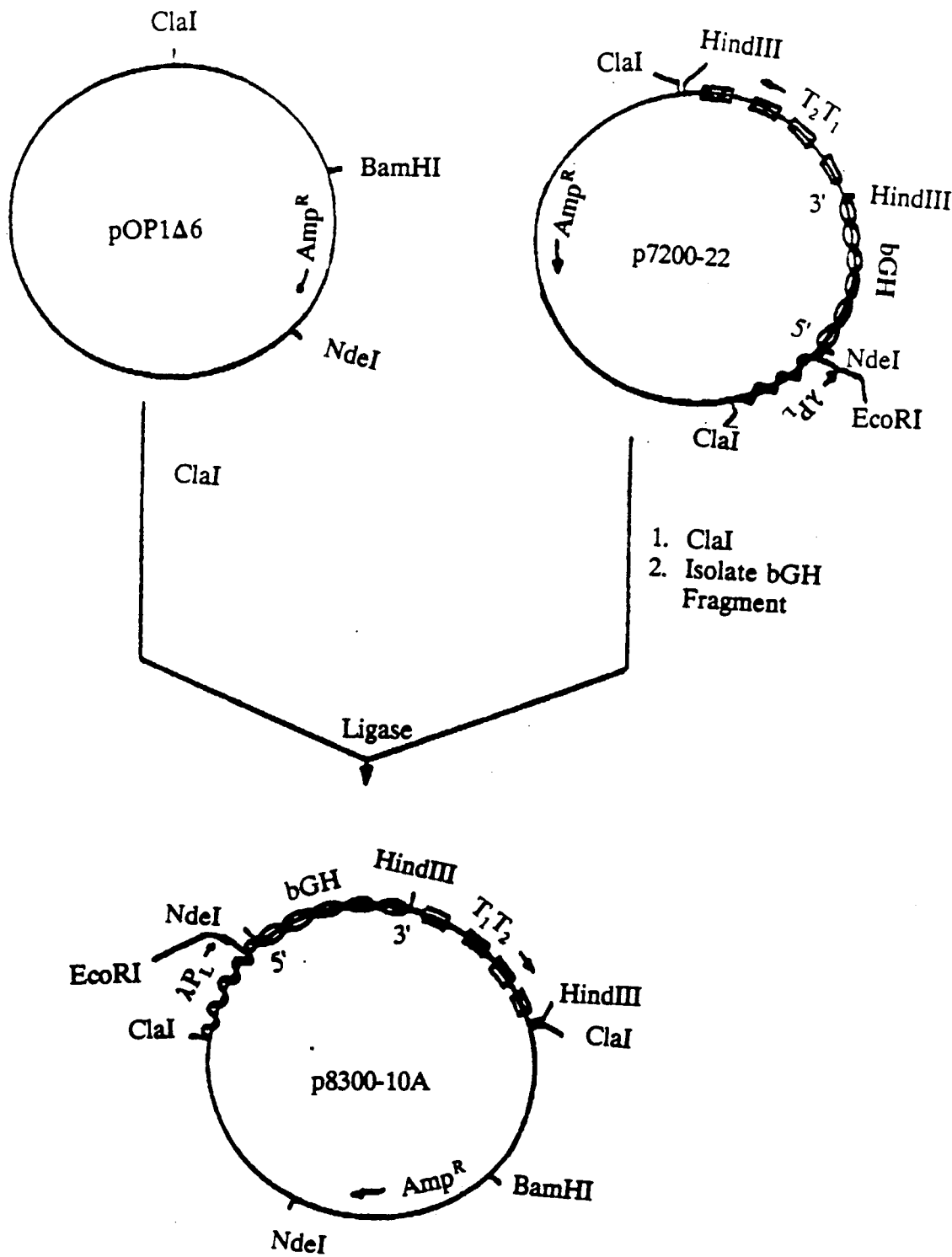

FIG. 7. Construction of p8300-10A.

The plasmid p8300-10(ATCC 39785) which expresses an analog of the natural phenylalanine form of bGH having methionine at the N-terminus (met-phe bGH) was prepared as follows. The plasmid p7200-22 contains the λP$_L$ promoter and ribosomal binding site derived from pJH200 (ATCC No. 39783), DNA encoding met-phe bGH and the T$_1$T$_2$rRNA termination sequences. The ClaI-ClaI fragment containing the λP$_L$ promoter, the C$_{II}$ ribosomal binding site, the met-phe bGH gene and the T$_1$T$_2$ transcription termination sequences was inserted into the unique ClaI site of plasmid pOP1Δ6, a constitutive high copy number plasmid, to form p8300-10A.

Figure 8:
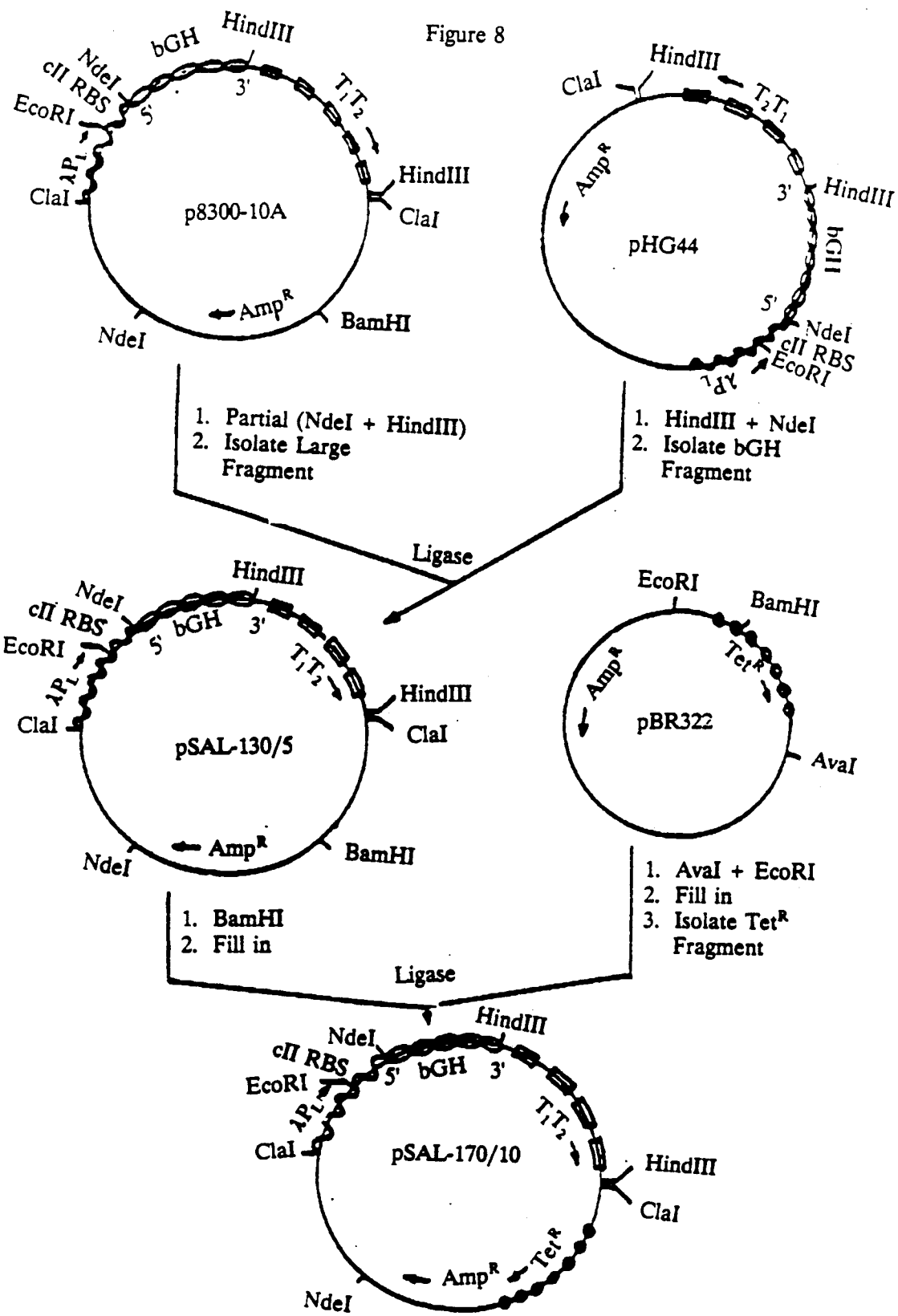

FIG. 8. Construction of pSAL-130/5 and pSAL-170/10.

The plasmid pHG44 (ATCC No. 39806) expressing met-asp-gln bGH protein was digested with NdeI and HindIII. The resulting NdeI-HindIII bGH fragment was isolated and ligated to a fragment from p8300-10A (ATCC No. 39785) prepared by partial digestion with both NdeI and HindIII. Such a ligation replaces the met-phe bGH gene fragment with the met-asp-gln bGH gene fragment. The plasmid so obtained, pSAL-130/5, expresses rec bGH. pSAL-170/10 was obtained by treating the EcoRI-AvaI fragment containing the Tet$^R$ gene of pBR322 plasmid (ATCC No. 37017) with DNA polymerase I (Klenow) and inserting it into pSAL-130/5 which had been digested with BamHI and filled in with DNA polymerase I (Klenow).

Figure 9:
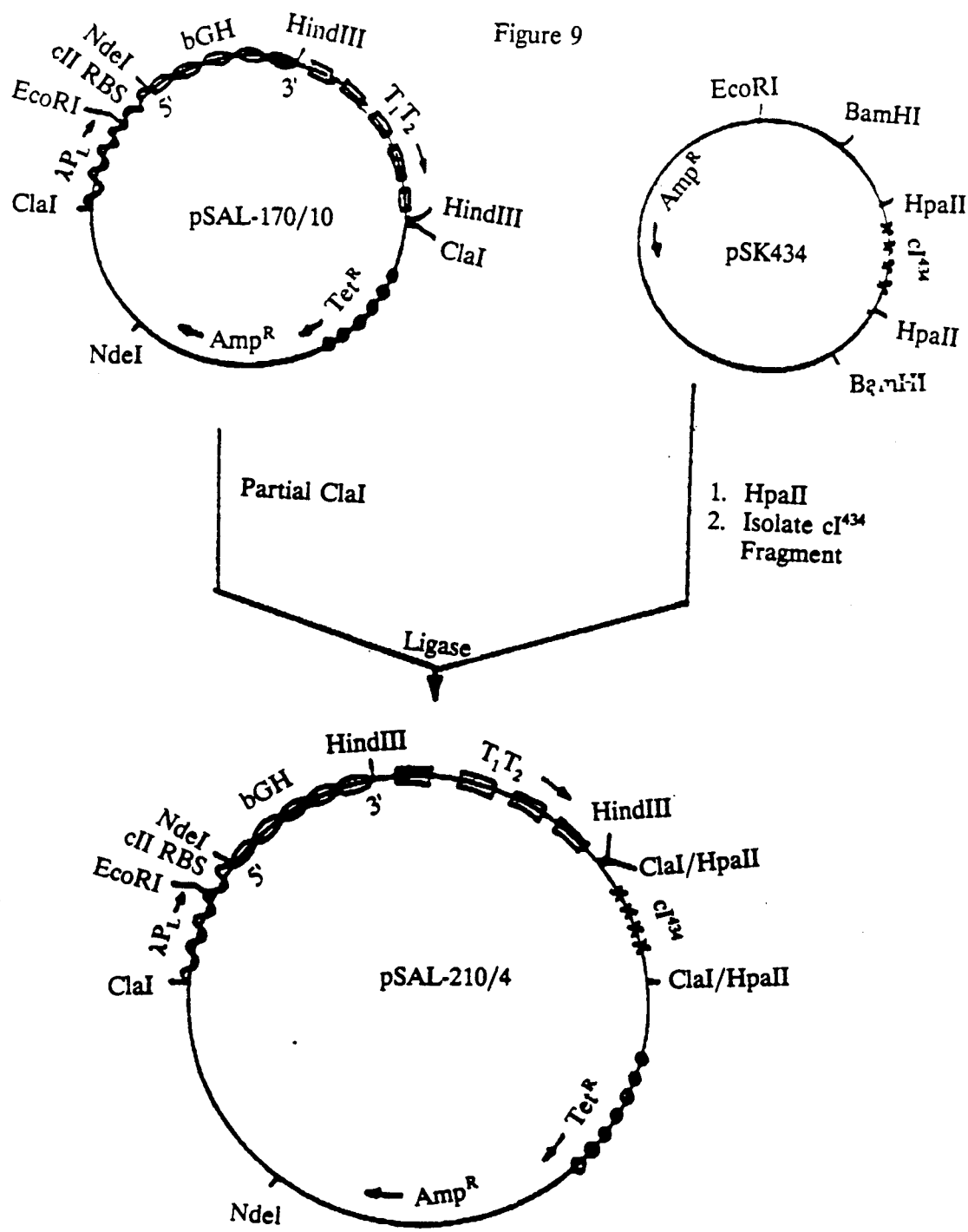

FIG. 9. Construction of pSAL-210/4.

Linear form DNA (form III) was prepared by partial ClaI digestion of pSAL-170/10. It was purified from an agarose gel and ligated to a HpaII-HpaII cI$^{434}$ gene fragment which was isolated from a HpaII digest of the plasmid pSK434 (ATCC No. 39784).

Figure 10:
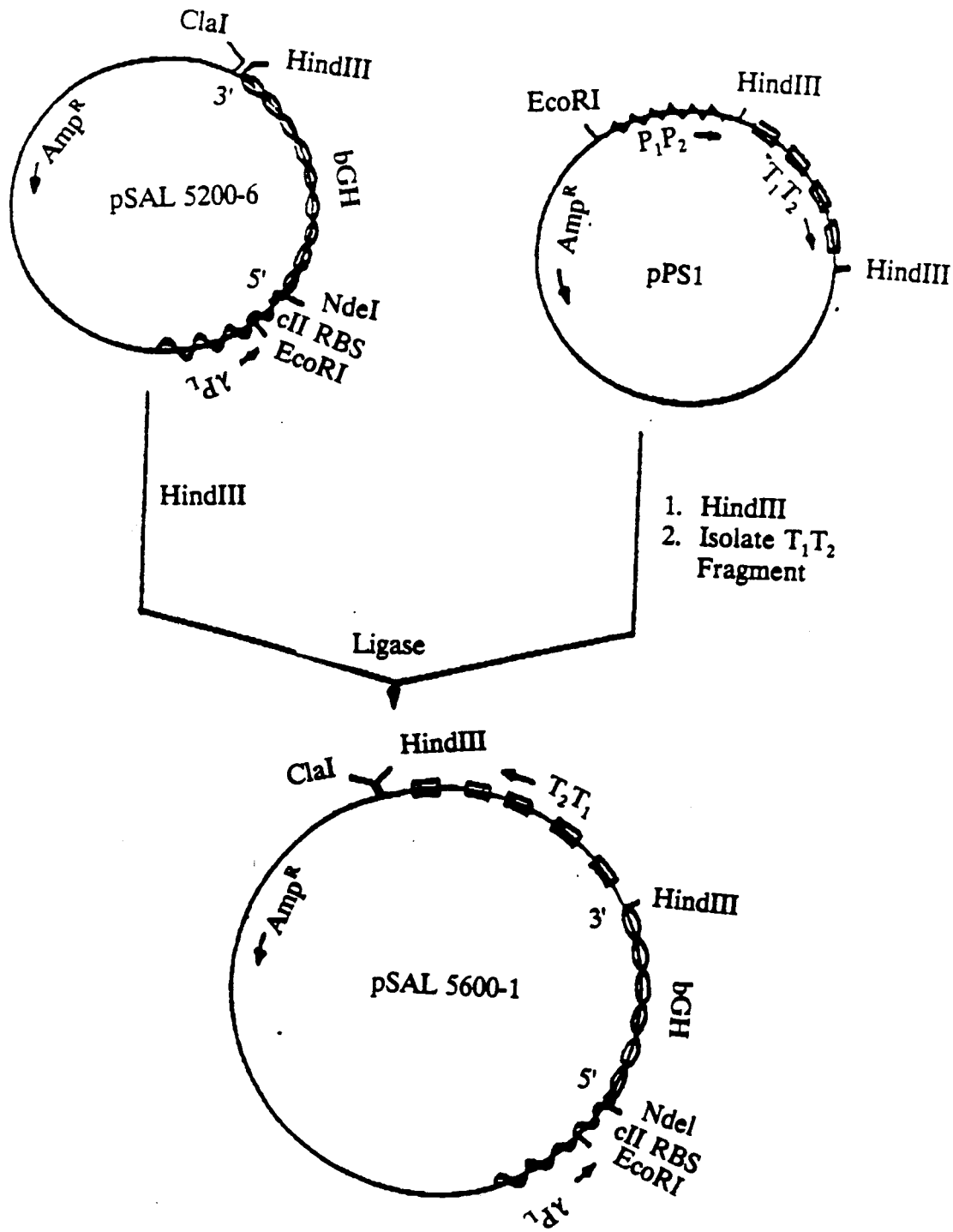

FIG. 10. Construction of pSAL 5600-1.

pSAL 5200-6 (FIG. 3) was digested with HindIII. The linear form DNA (form III) was purified from an agarose gel and ligated to a HindIII-HindIII fragment of about 1200 base pairs which contains the rRNA operon transcription termination sequences, T$_1$T$_2$. The T$_1$T$_2$ HindIII-HindIII fragment was isolated from the plasmid pPSl (ATCC No. 39807) which was digested with HindIII. The resulting plasmid pSAL 5600-1 contains the T$_1$T$_2$ sequences at the 3' end of the met-asp-gln bGH sequence.

Figure 11:
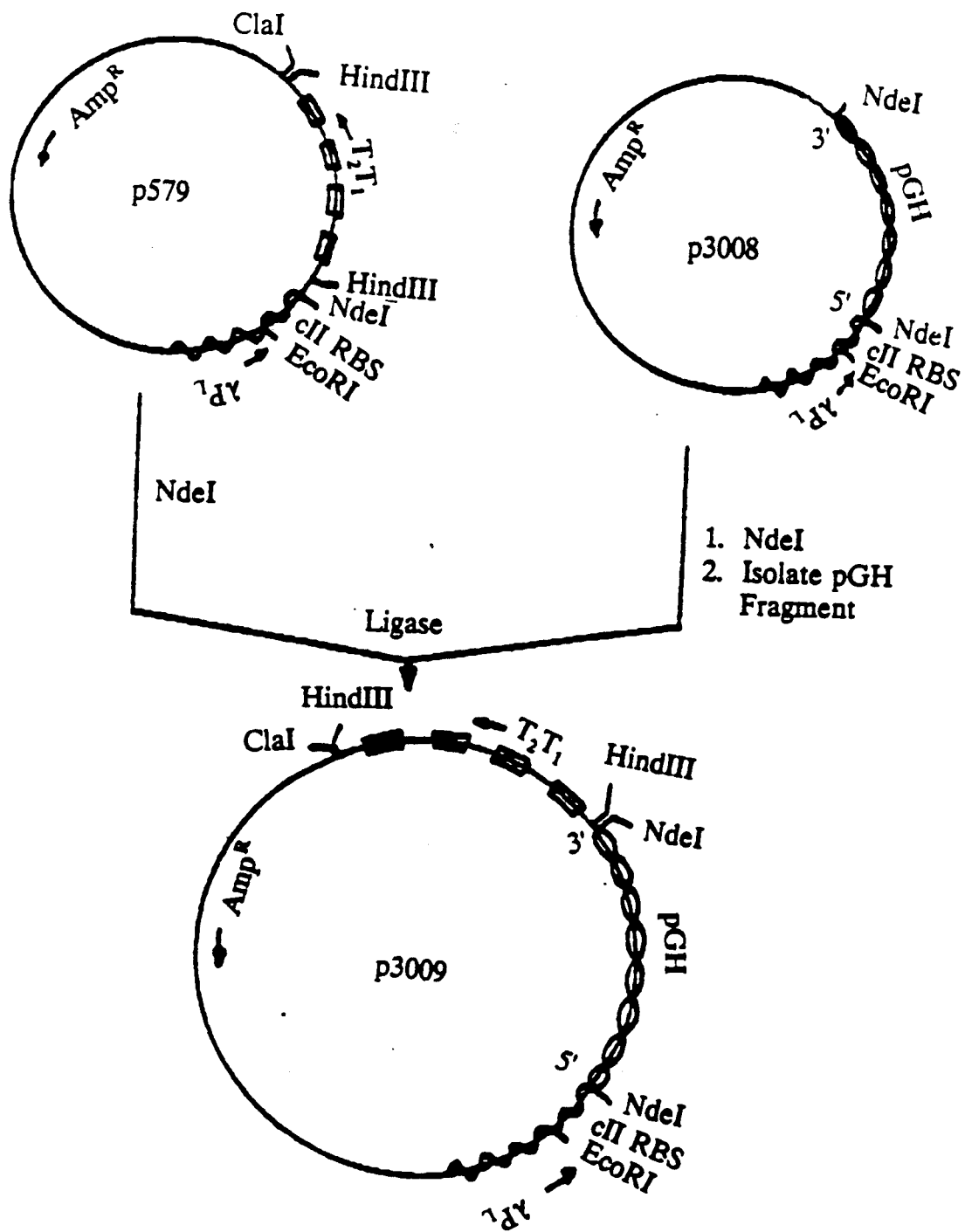

FIG. 11. Construction of p3009.

The NdeI-NdeI pGH fragment was isolated from plasmid p3008 (ATCC No. 39804) (FIG. 5). The fragment was inserted into the unique NdeI site of the expression vector p579 (FIG. 19) which had been digested with NdeI. The resulting plasmid p3009 expresses an analog of natural porcine growth hormone protein having a methionine residue added at the N-terminus.

Figure 12:
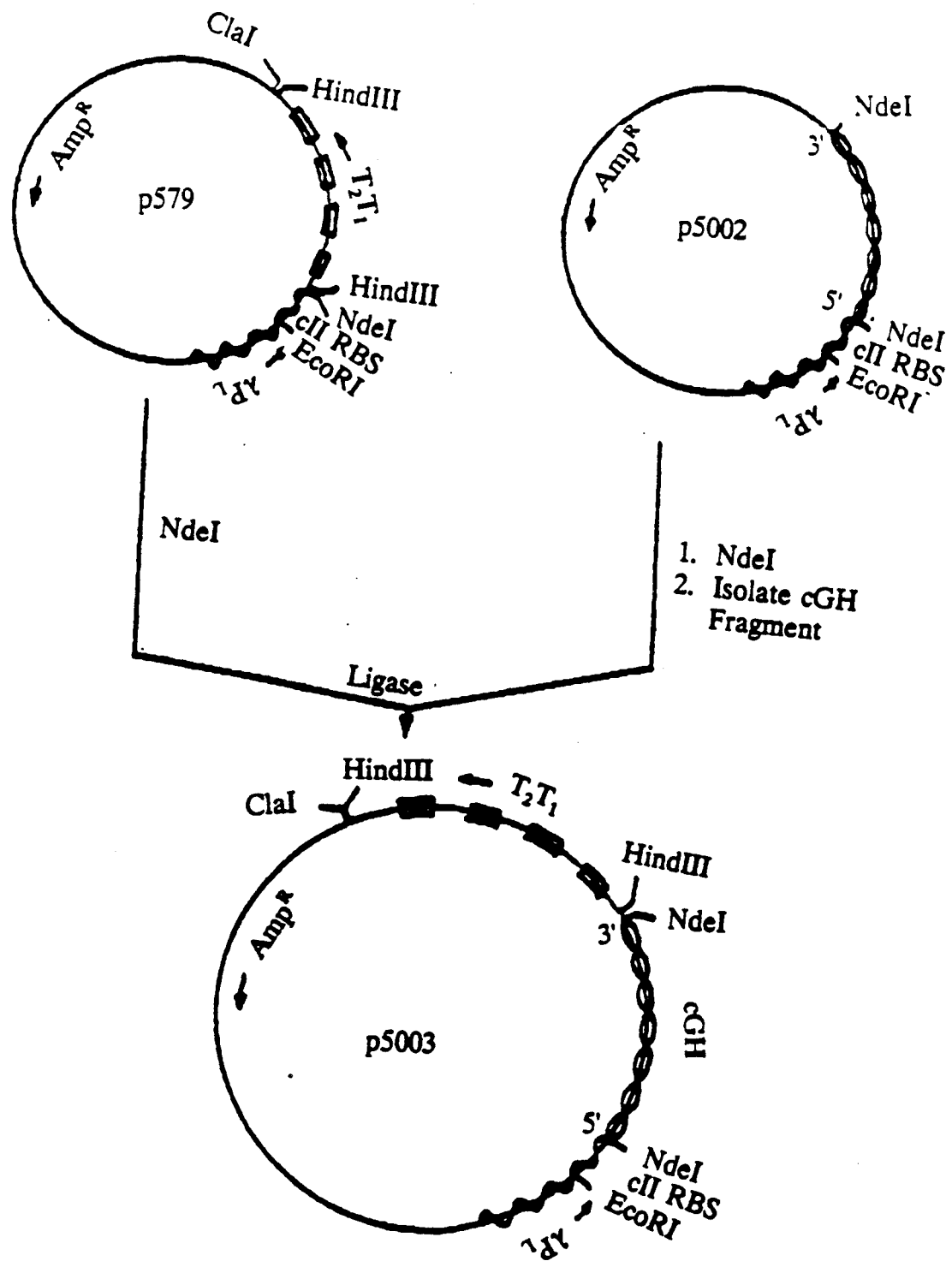

FIG. 12. Construction of p5003.

The NdeI-NdeI cGH fragment was isolated from plasmid p5002. The fragment was inserted into the unique NdeI site of the expression vector p579 (FIG. 19) which had been digested with NdeI. The resulting plasmid p5003 (ATCC No. 39792) expresses an analog of natural chicken growth hormone protein having a methionine residue added at the N-terminus.

Figure 13:
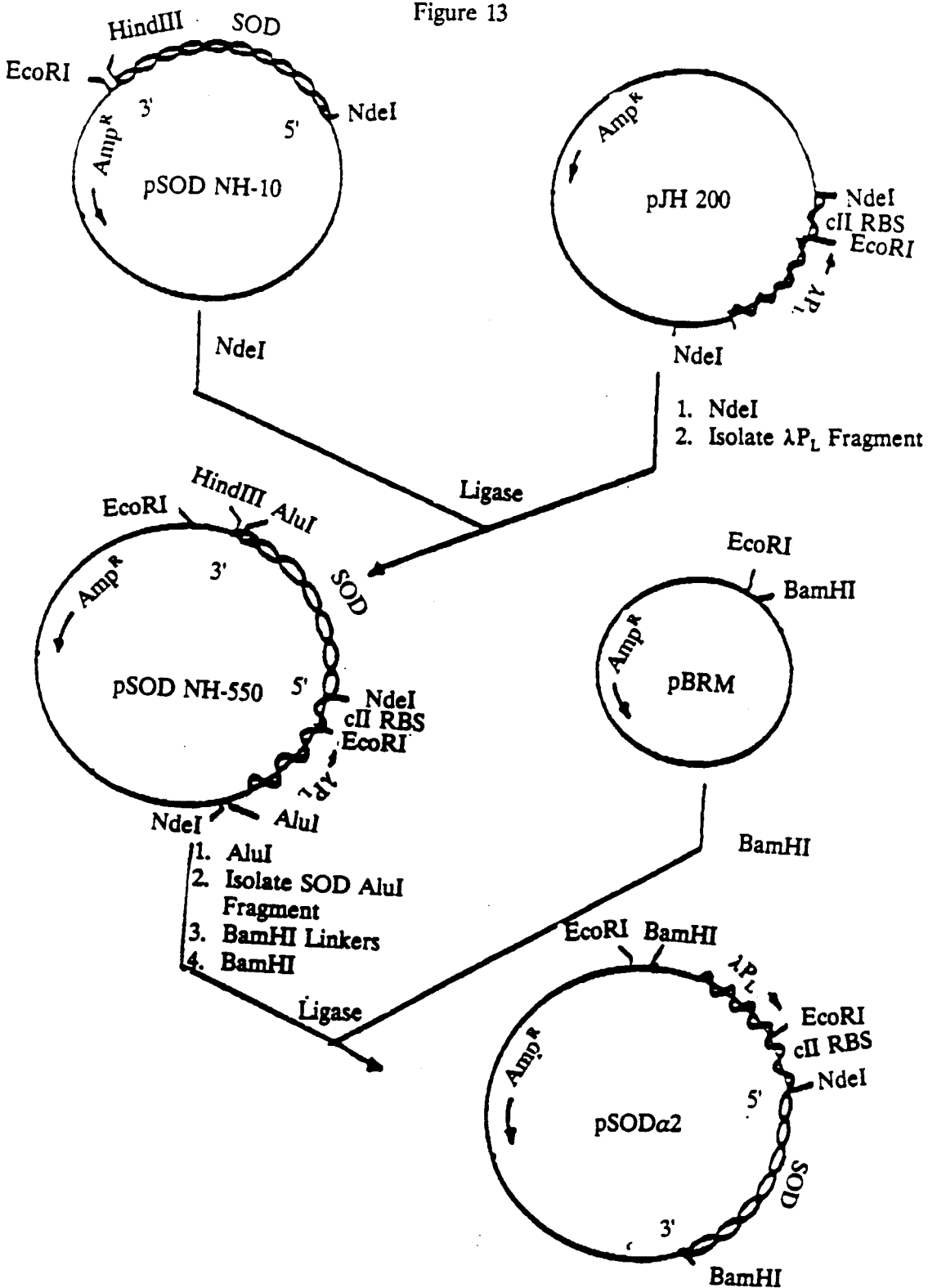

FIG. 13. Construction of pSODα2.

The pJH200 (ATCC No. 39783) expression vector was digested with NdeI. The 550 base pair NdeI fragment containing the λP$_L$ promoter and C$_{II}$ ribosomal binding site was isolated and inserted into the unique NdeI site of plasmid pSOD NH-10 which had been digested with NdeI. (Plasmid pSOD NH-10 is derived from a cDNA clone of human SOD [Lieman-Hurwitz, J., et al., PNAS (1982) 79: 2808]) The resulting plasmid pSOD NH-550 was digested with AluI. (Only the relevant AluI site is shown in the figure.) The large AluI fragment containing the λP$_L$ promoter and the SOD gene was isolated. BamHI linkers were attached and the resulting fragment was digested with BamHI. The BamHI digestion product was inserted into the unique BamHI site of pBRM (ATCC No. 37283) to form pSODα2 (ATCC No. 39786).

Figure 14:
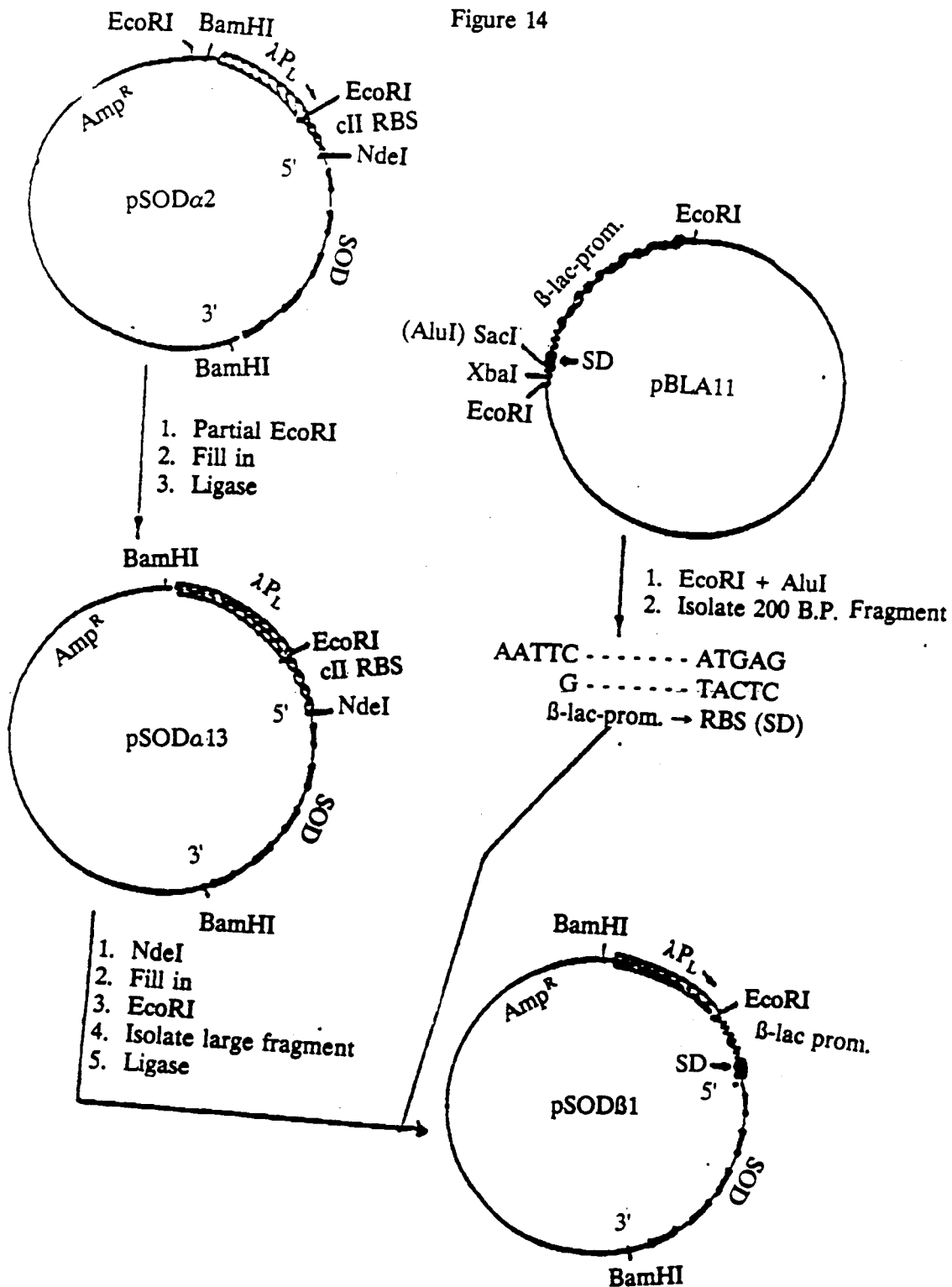

FIG. 14. Construction of pSODα13 and pSODβ1.

The plasmid pSODα2 (ATCC No. 39786) was partially digested with EcoRI and the resulting linear form DNA was isolated from an agarose gel. The purified DNA was filled in with DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSODβ1 contains the ribosomal binding site of the β-lactamase gene and the λP$_L$ promoter.

Figure 15:
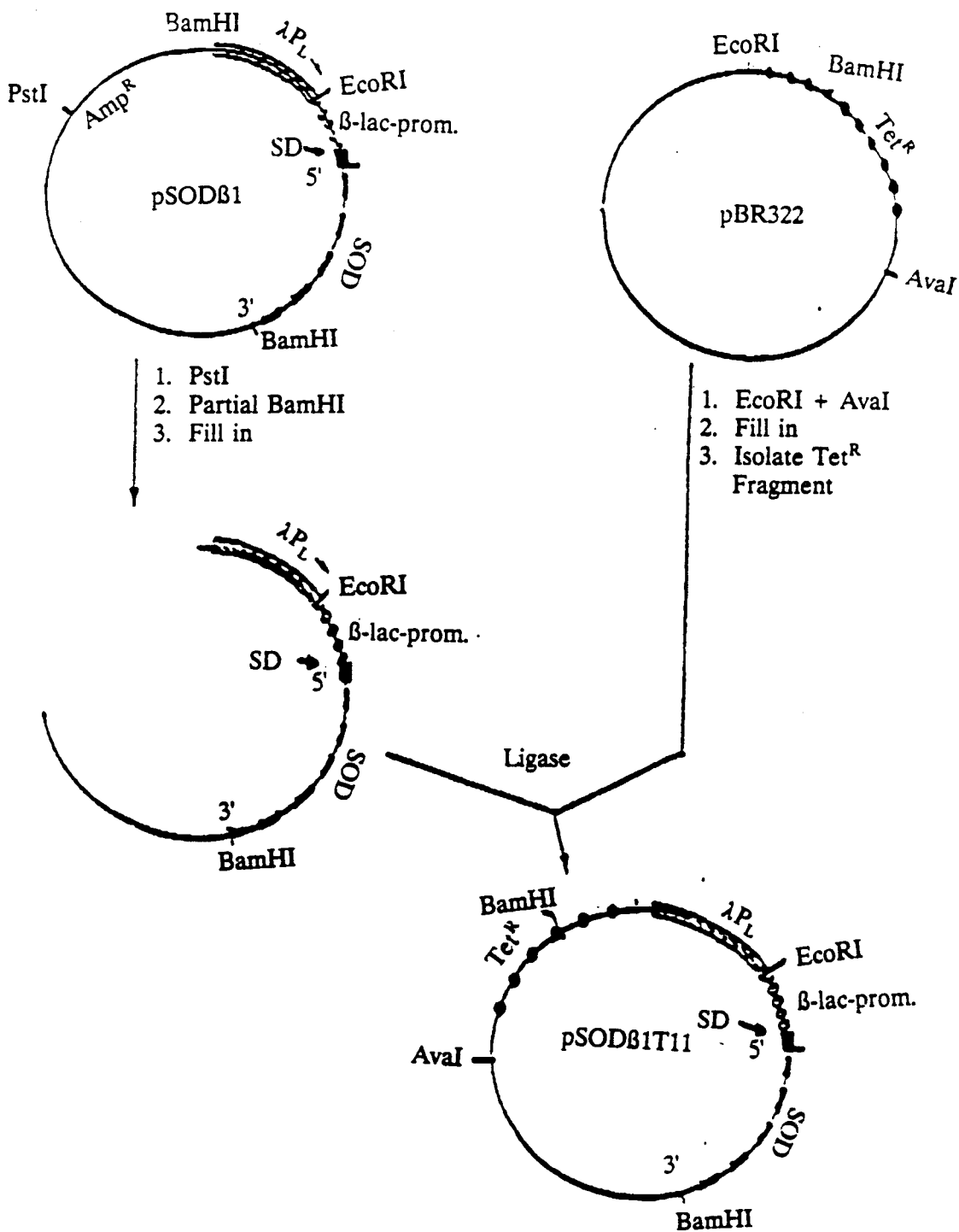

FIG. 15. Construction of pSODβ$_1$T$_{11}$.

Plasmid pBR322 (ATCC No. 37017) was digested with EcoRI and AvaI. The resulting DNA was filled in with DNA polymerase I (Klenow). The Tet$^R$ gene fragment was then isolated and ligated to the large fragment isolated from pSODβ1 (FIG. 14) plasmid which had been digested with PstI followed by a partial BamHI digest and then filled in with DNA polymerase I (Klenow). The resulting plasmid pSODα$_1$T$_{11}$ contains the Tet$^R$ gene.

Figure 16:
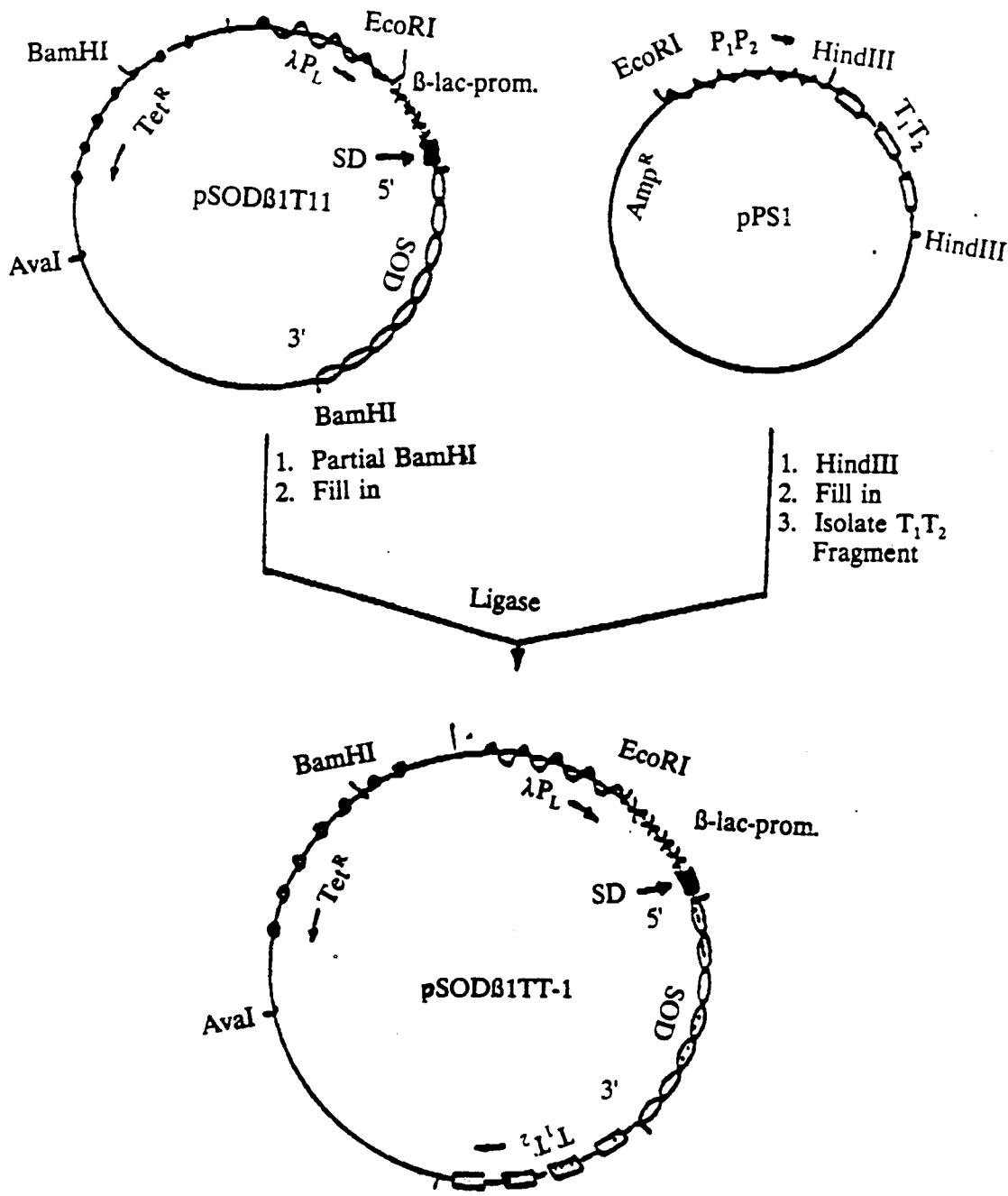

FIG. 16. Construction of pSODβ$_1$TT-1.

The rRNA T$_1$T$_2$ transcription termination fragment was isolated from plasmid pPSl (ATCC No. 39807) which had been digested with HindIII and filled in with DNA polymerase I (Klenow). The fragment was ligated to plasmid pSODβ$_1$T$_{11}$ (FIG. 15) which had been partially digested with BamHI and filled in with DNA polymerase I (Klenow).

Figure 17:
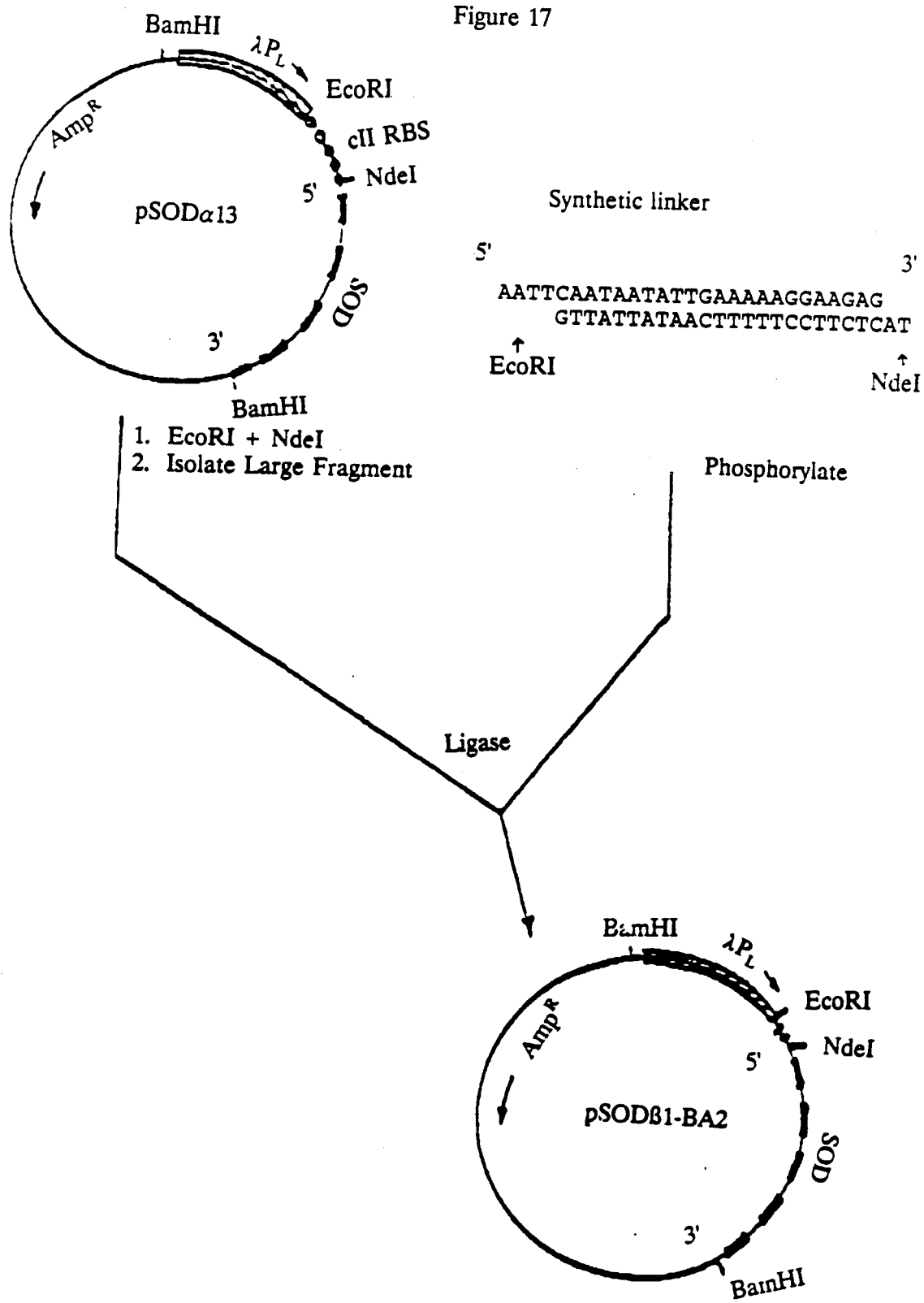

FIG. 17. Construction of pSODβ$_1$-BA2.

A synthetic DNA fragment with the sequence:

5'-AATTCAATAATATTGAAAAAGGAAGAG-3'
GTTATTATAACTTTTTCCTTCTCAT which is similar to the sequence of the natural β-lactamase ribosomal binding site, was phosphorylated and ligated to the large fragment of pSODα13 plasmid (FIG. 14) which had been digested with NdeI and EcoRI.

Figure 18:
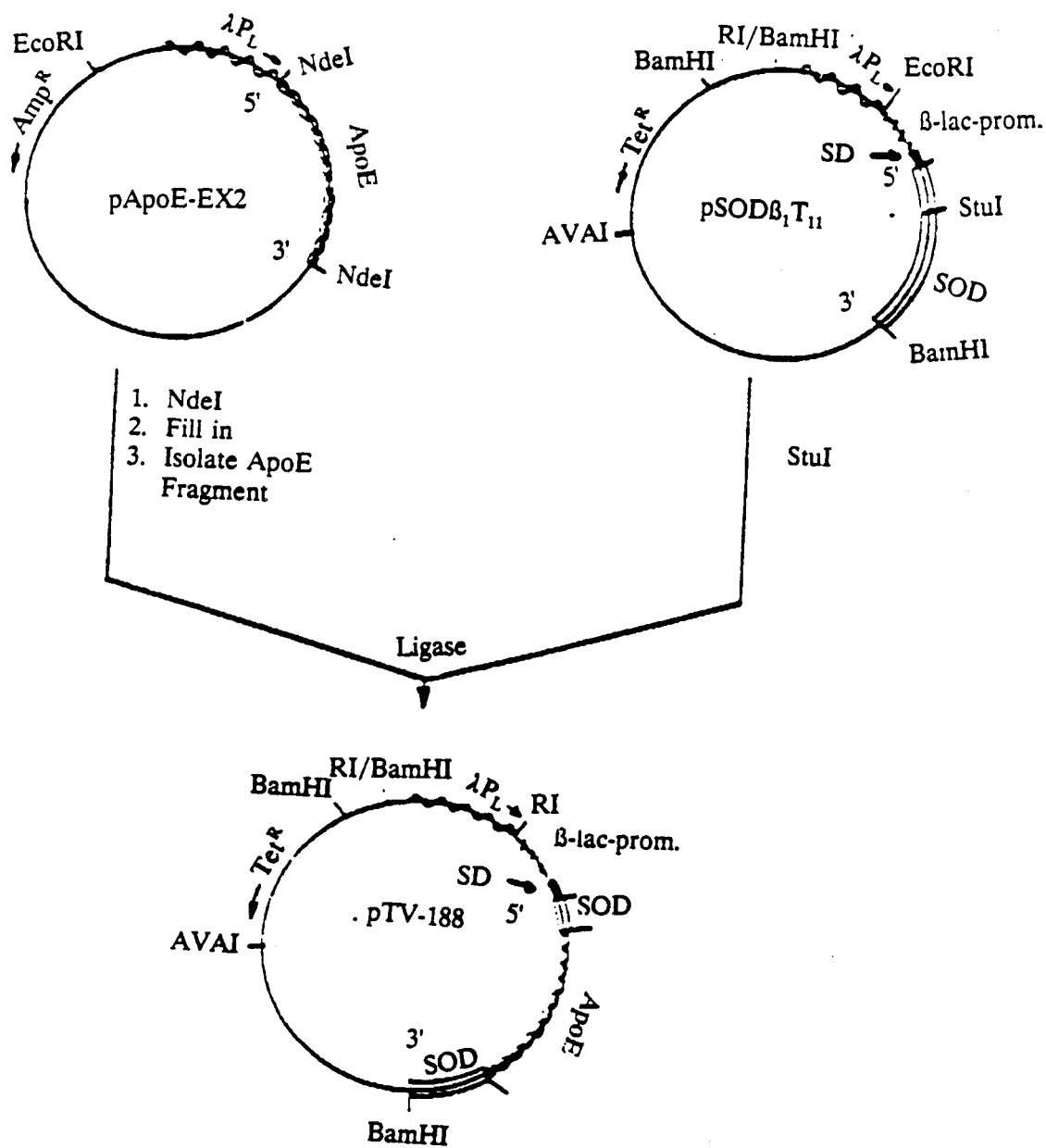

FIG. 18. Construction of pTV-188.

Plasmid pApoE-EX2 (ATCC No. 39787) was digested with NdeI and then fragments filled in with DNA polymerase I (Klenow). The resulting ApoE gene fragment was isolated and inserted into the unique blunt end StuI site of the pSODβ$_1$T$_{11}$ plasmid (FIG. 15). The resulting plasmid pTV-188 expresses an ApoE fused protein.

Figure 19:
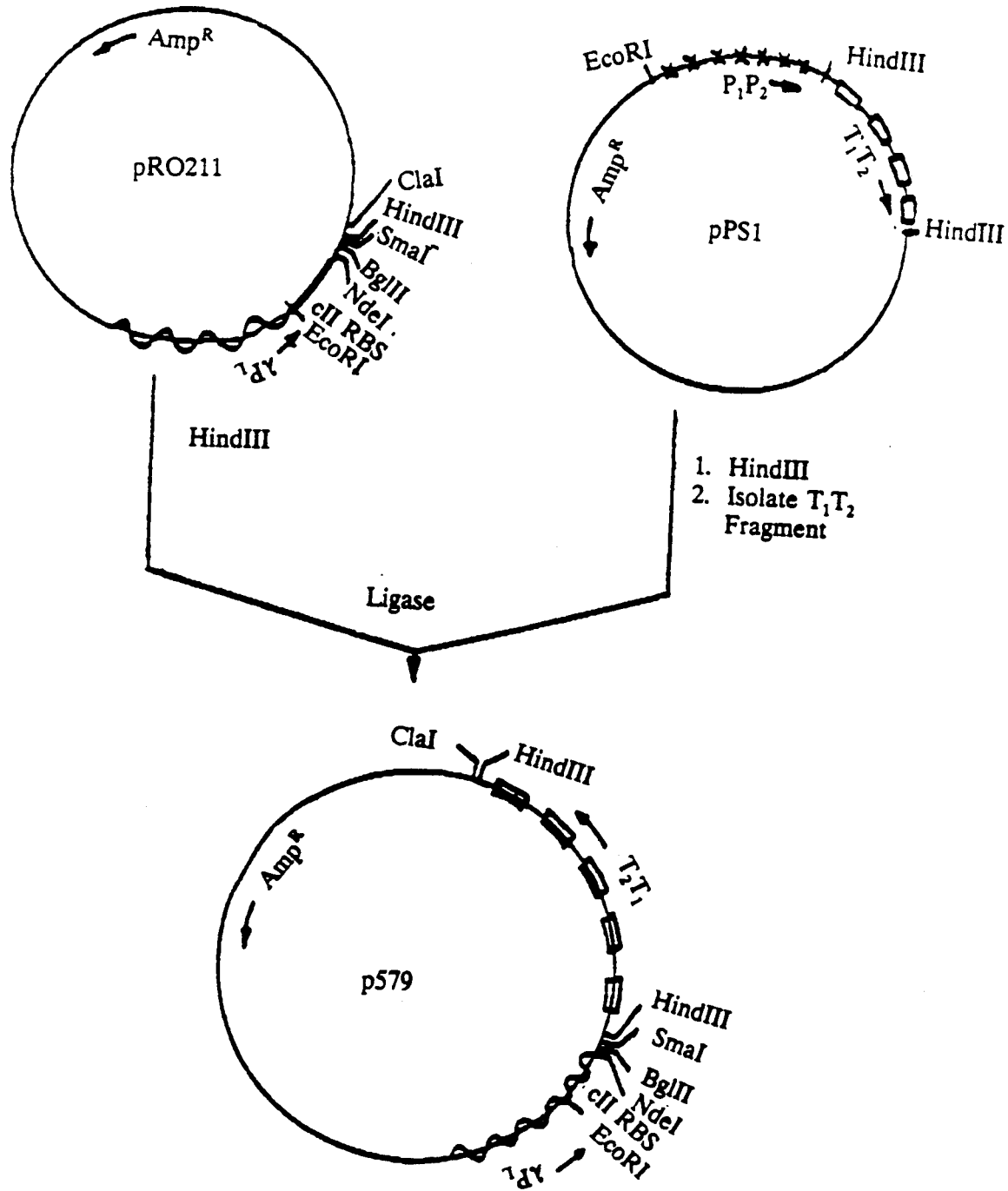

FIG. 19. Construction of p579.

The rRNA operon T$_1$T$_2$ transcription termination fragment was isolated from plasmid pPSl (ATCC No. 39807) which had been digested with HindIII. The $T_1T_2$ fragment was inserted into the unique HindIII site of pRO211 (FIG. 2) which had been digested with HindIII. The resulting expression vector, p579, contains the $\lambda P_L$ promoter, the $C_{II}$ ribosomal binding site, followed by the $T_1T_2$ transcription termination signals.

Figure 20:
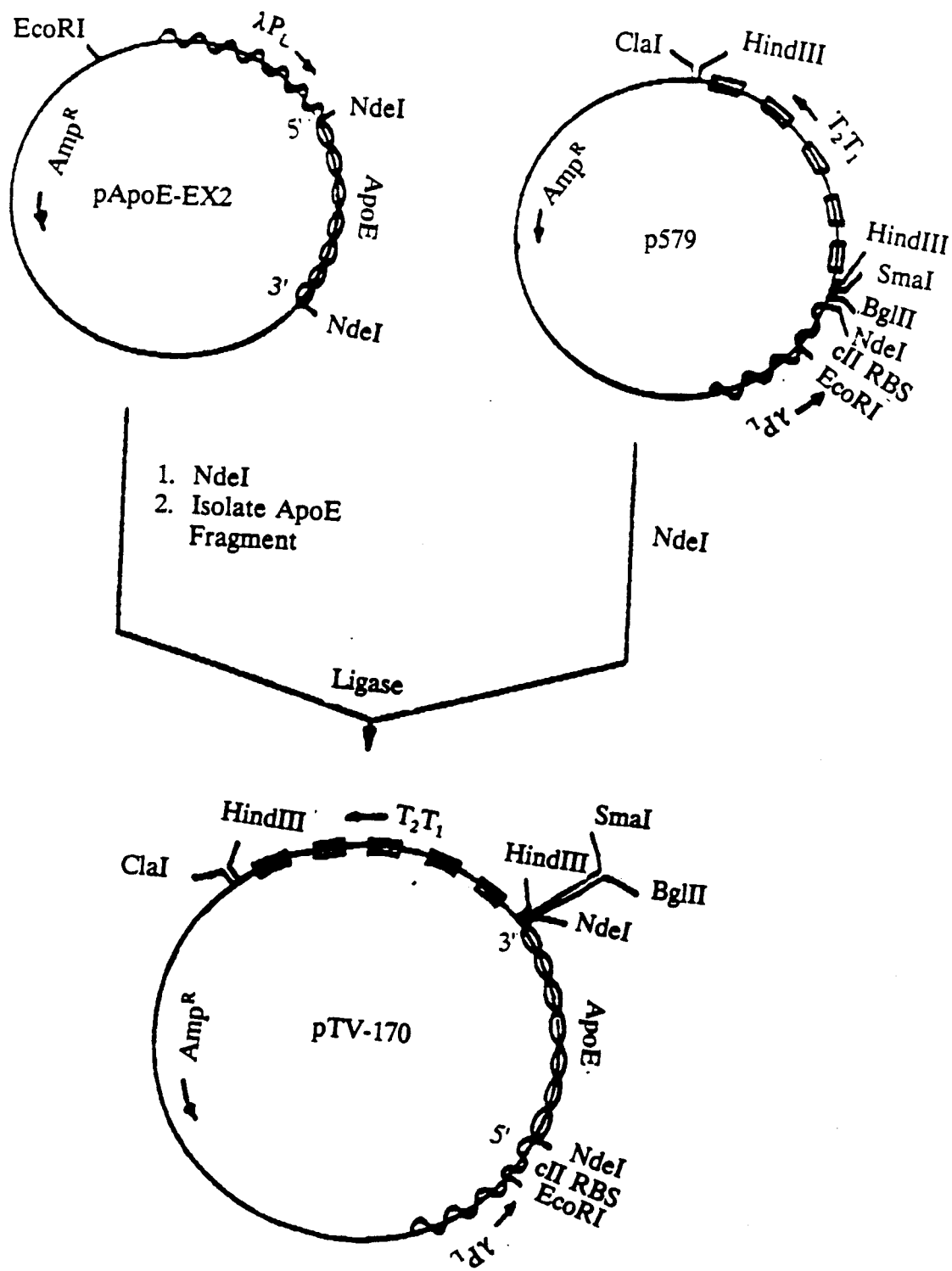

FIG. 20. Construction of pTV-170.

The NdeI-NdeI ApoE fragment was isolated from plasmid pApoE-EX2 (ATCC No. 39787) and inserted into the unique NdeI site of the expression vector p579 (FIG. 19) which had been digested with NdeI. The resulting plasmid pTV-170 expresses an analog of natural human ApoE protein having a methionine residue added at the N-terminus.

Figure 21:
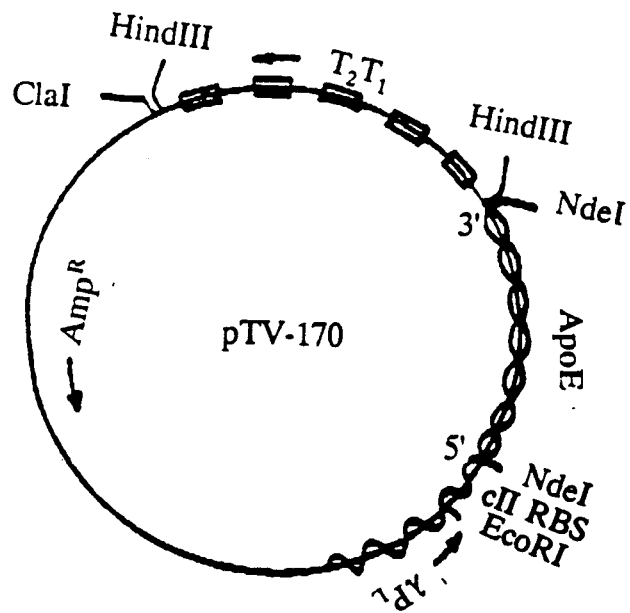
Figure 21:
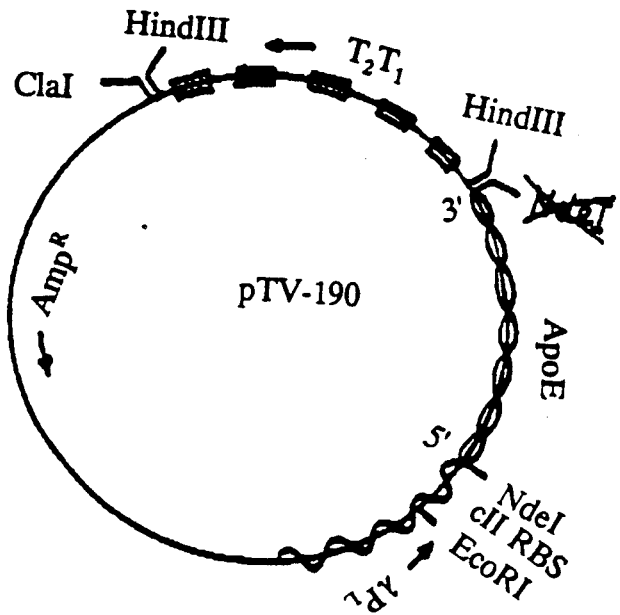

FIG. 21. Construction of pTV-190.

The plasmid pTV-170 (FIG. 20) was partially digested with NdeI and filled in with DNA polymerase I (Klenow). The isolated linear form DNA was religated to yield the plasmid pTV-190 which was analyzed and found to have only one NdeI site at the 5' end of the ApoE gene.

Figure 22:
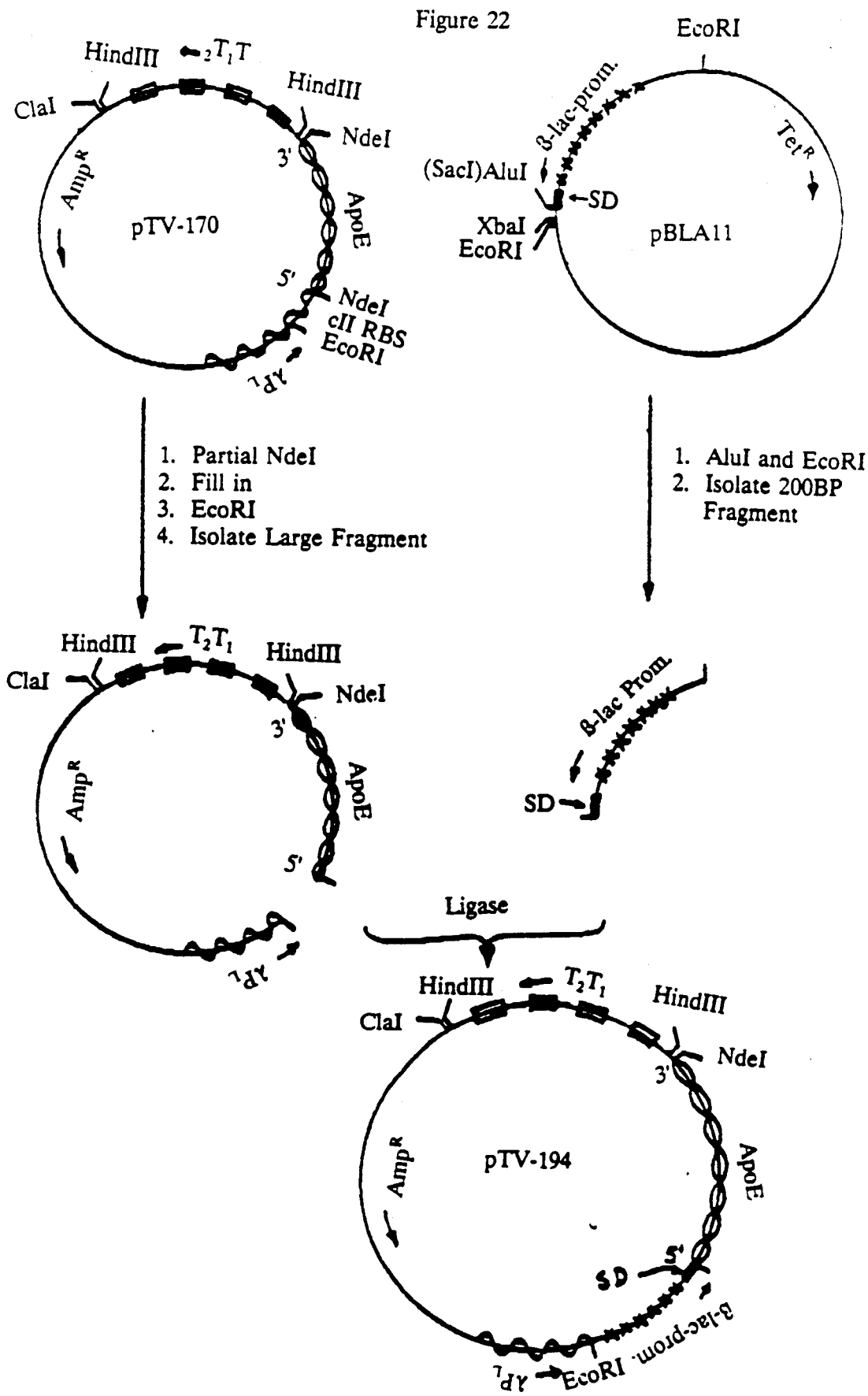

FIG. 22. Construction of pTV-194.

The β-lactamase promoter and ribosomal binding site fragment was isolated from plasmid pBLA11 (ATCC No. 39788) after digestion with EcoRI and AluI. This fragment was ligated to the large fragment of pTV-170 (FIG. 20) plasmid which had been digested with NdeI, filled in with DNA polymerase I (Klenow) and then digested with EcoRI.

Figure 23:
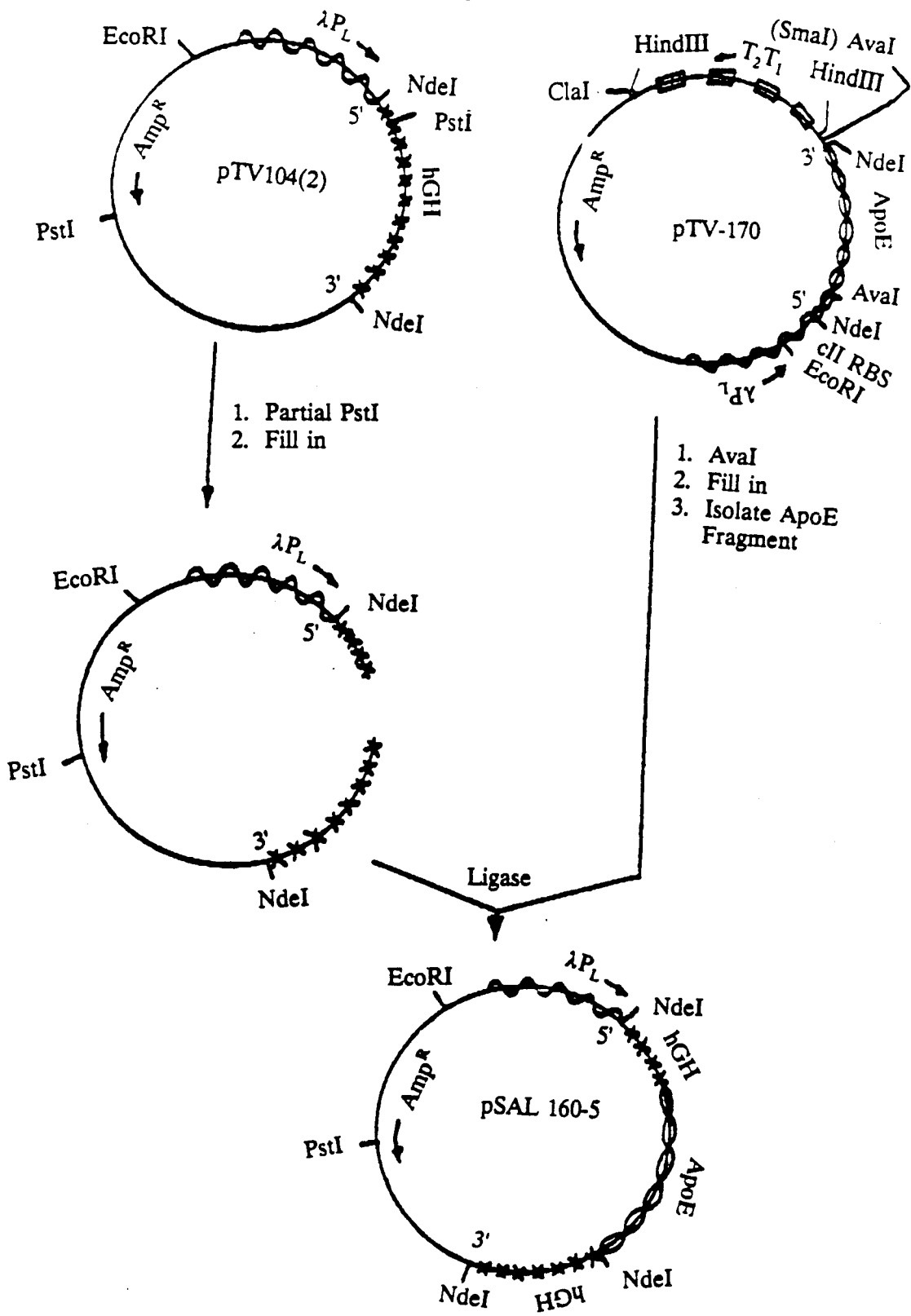

FIG. 23. Construction of pSAL 160-5.

An AvaI-AvaI fragment containing the ApoE DNA sequence was isolated from pTV-170 (FIG. 21) which was digested with AvaI. The fragment was filled in with DNA polymerase I (Klenow) and isolated on agarose gel. The purified ApoE fragment was inserted into the PstI site of the pTV 104(2) plasmid (ATCC No. 39384) which was partially digested with PstI and filled in with DNA Polymerase I (Klenow). The resulting plasmid is designated pSAL 160-5.

Figure 24:
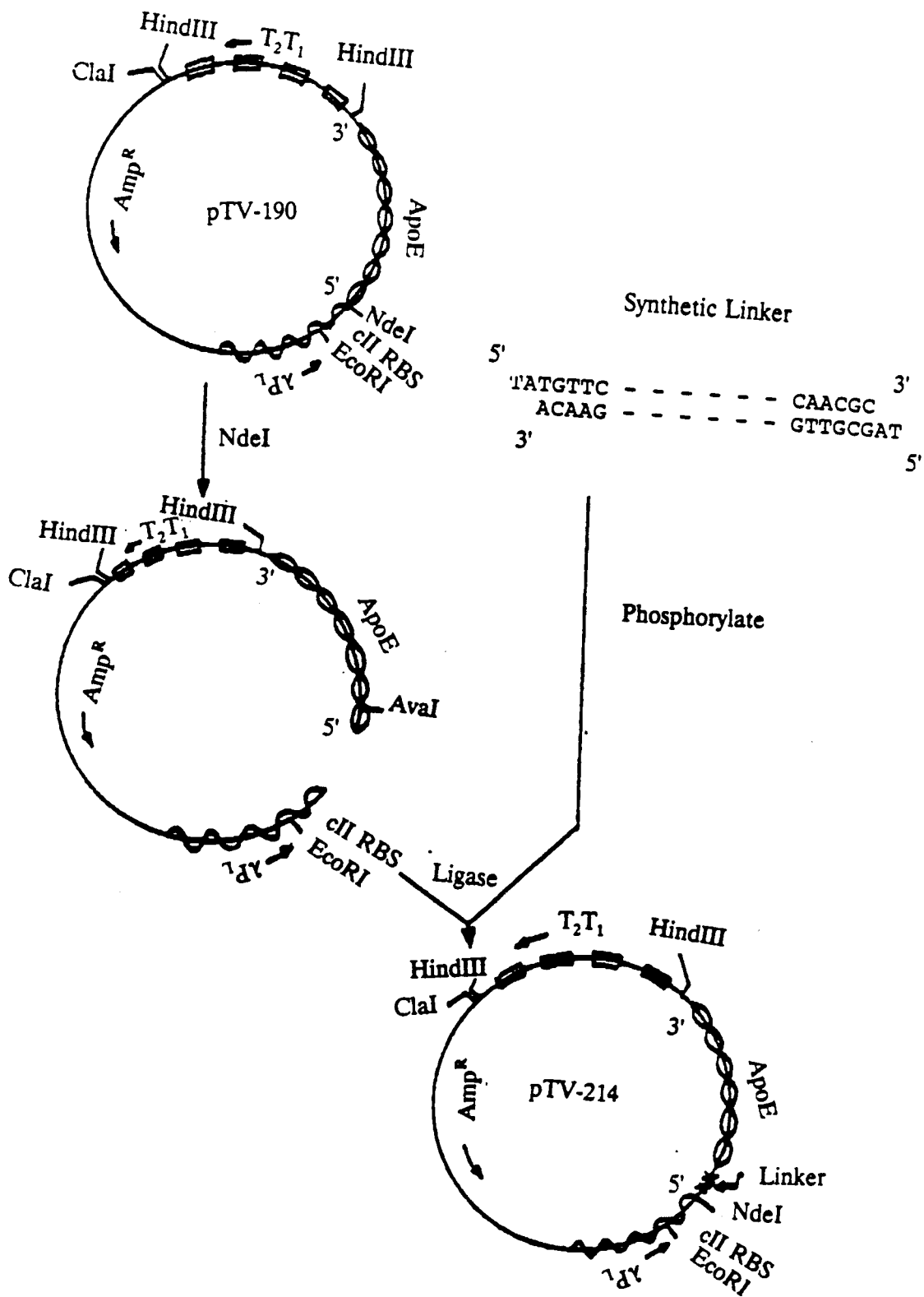

FIG. 24. Construction of pTV-214.

A synthetic fragment containing the first 14 amino acids of human growth hormone with the sequence:

```
TATGTTCCCAACCATTCCATTATCCCGTCTGTTCGACAACGC
 ACAAGGGTTGGTAAGGTAATAGGGCAGACAAGCTGTTGCGAT
``` was phosphorylated using $\gamma$-$^{32}$P-ATP and polynucleotide kinase. The phosphorylated linker was inserted into the unique NdeI site of pTV-190 plasmid which had been digested with NdeI.

DETAILED DESCRIPTION OF THE INVENTION

A vector has been developed which enables the achievement of enhanced levels of gene expression and polypeptide production. The vector is a double-stranded DNA molecule. Upon introduction into a suitable bacterial host cell containing the thermolabile repressor $C_I$ the vector renders the host cell capable, upon increasing the temperature of the host cell to a temperature at which the repressor is inactivated, of effecting expression of a desired gene inserted into the vector and production of polypeptide encoded by the gene.

The vector includes in 5' to 3' order the following:

a DNA sequence which contains the promoter and operator $P_LO_L$ from lambda bacteriophage;

the N utilization site for binding antiterminator N protein;

a first restriction enzyme site permitting replacement of the DNA sequence containing the ribosomal binding site which follows thereafter;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a second restriction enzyme site for inserting the desired gene into the vector in phase with the ATG initiation codon; and a DNA sequence which contains a $T_1T_2$ rRNA transcription termination sequence.

The vector also includes a DNA sequence which contains an origin of replication from a bacterial plasmid capable of autonomous replication in the host cell and a DNA sequence which contains the fragment designated $cI^{434}$ The $cI^{434}$ fragment includes the gene for the $cI^{434}$ repressor protein and its associated promoter and operator. $cI^{434}$ represses a $cI^{434}$-lysogen; loss of the plasmid will result in cell lysis. The distance between the 3' end of the $P_LO_L$ promoter and operator sequence and the 5' end of the N utilization site is less than about 150 base pairs and the distance between the 3' end of the N utilization site and the 5' end of the ribosomal binding site is less than about 50 base pairs.

Another component of the vector is a first restriction enzyme site permitting replacement of the DNA sequence containing the ribosomal binding site which follows thereafter. Numerous such sites may be used. Suitable sites include EcoRI.

Yet another component of the vector is a second restriction enzyme site for insertion of desired genes into the vector in phase with the ATG initiation codon. Numerous such sites may be used. Suitable sites include NdeI, ClaI, HindIII, SmaI, BglII, XbaI, SacI and AluI.

Generally it is desirable that the second restriction enzyme site also function as the second restriction site necessary to permit replacement of the DNA sequence containing the ribosomal binding site. If the second restriction site is not also used for this purpose then the vector of this invention must also include a third restriction enzyme site after the ribosomal binding site but prior to the second restriction site.

Preferably, the vector contains two unique restriction enzyme sites. The first site permits replacement of the DNA sequence containing the ribosomal binding site. The second site permits insertion of the desired gene into the vector in phase with the ATG initiation codon. In a presently preferred embodiment, EcoRI is the first restriction enzyme site and NdeI is the second restriction enzyme site.

A further component of the vector is a $T_1T_2$ rRNA termination sequence. Preferably, the $T_1T_2$ rRNA termination sequence is less than about 100 base pairs from the 3' end of the second restriction enzyme site. More preferably rRNA termination sequence is less than about 20 base pairs from the 3' end of the second restriction enzyme site.

The vector also includes the $cI^{434}$ repressor gene which represses a $\lambda$imm434cI- lysogen. When the $cI^{434}$ repressor gene is contained within a host, $\lambda$imm434cI$^-$ prophage induction and subsequent lysis is prevented.

Thus, there is no need to use expensive antibiotic selection salines when cI[434] is present.

Preferably, the vector includes a DNA sequence which contains a gene associated with a selectable or identifiable phenotypic trait which is manifested when the vector is present in the host cell.

The preferred host for use with the vector is *Escherichia coli*. The presently preferred strains are A1637, A1645, (C600r⁻m⁺gal⁺thr⁻leu⁻lac⁻[λcI857ΔH1-ΔBam N+]) A2602, A2097 A1563 and A1645 (λi43-4cI⁻mini Tn10). A1645(λi434 cI⁻ $^{mini\ Tn}$10) is presently the most preferred strain. It has been deposited with the American Type Culture Collection in Rockville, Md., U.S.A. containing plasmid pHG50. All of the deposits mentioned herein were made pursuant to the Budapest Treaty on the International Recognition of the Deposit of Microorganisms except that pBR322 and pBRM are fully available from the American Type Culture Collection as ATCC Nos. 37017 and 37283, respectively, and D4 was deposited under ATCC No. 31826 in connection with the filing of a U.S. patent application.

A1645 was obtained from A1637 by selection for Gal+ (ability to ferment galactose) as well as loss of tetracycline resistance. It still contains the lambda expression system but part of the transposon has been removed by selection. Its phenotype is C600 r⁻m⁺gal+thr⁻leu⁻lac⁻(λcI857 ΔH1ΔBam N+).

A1645 (λi434 cI⁻mini Tn10) was derived by infecting *Escherichia coli* strain A1645 containing a plasmid with λimm434 cI[3008] mini Tn10Δ16Δ17 at 30° C. Tetracycline resistant colonies were isolated and purified. The strain containing plasmid pHG50 has been deposited with the American Type Culture Collection under ATCC No. 39805.

A2602 and A1563 are derived from SA500. Their phenotypes are SA500 his⁻ile⁻gal+Δ8(λCI857 ΔH1 ΔBam N+ and SA500 his⁻ile⁻gal+Δ8 lac ZxA21 (λCI859 int2 xisl nutL3 ΔH1), respectively. A2097 is derived from A1645. Its phenotype is A1645 lac ΔXA21 proC:Tn10.

Preferably, the vector is a covalently closed circular double-stranded molecule. However, it is not essential that the vector be covalently closed.

The vector achieves its enhanced expression levels after the host cell is heated to a temperature at which the $C_I$ repressor protein is destroyed. A temperature above about 38° C. is effective for this purpose and since it is desired that unnecessary heat damage to the host cells be avoided to as great an extent as possible, it is generally desirable that the temperature not exceed 42° C. by more than a few degrees.

One important component of the vector is the ribosomal binding site. Suitable sites are $C_{II}$ from lambda bacteriophage having the sequence:

TAAGGAAATACTTACAT
ATTCCTTTATGAATGTA;

a mutant of $C_{II}$ from lambda bacteriophage having the sequence:

TAAGGAAGTACTTACAT
ATTCCTTCATGAATGTA;

the major head protein gene of bacteriophage lambda having the sequence:

TTTTTTTACGGGATTTTTTTATG
AAAAAAATGCCCTAAAAAAATAC;

the natural β-lactamase ribosomal binding site derived from pBR322;

a synthetic oligonucleotide having the sequence:

AATTCGAGCGCAAGGAAACAGGCTCA
GCTCGCGTTCCTTTGTCCGAGTAT;

a synthetic oligonucleotide having the sequence:

AATTCAATAATATTGAAAAAGGAAGAG
GTTATTATAACTTTTTCCTTCTCAT; and a natural ribosomal binding site derived from *Bacillus thurengensis*.

The vector also includes an origin of replication from a bacterial plasmid capable of autonomous replication in the host cell. Suitable such origins of replication may be obtained from a number of sources, e.g., from pBR322 or pR1.

A DNA sequence which contains a gene associated with a selectable or identifiable phenotypic trait which is manifested when the vector is present in the host cell is also a component of the vector. Suitable genes include those associated with temperature sensitivity or drug resistance, e.g., resistance to ampicillin, chloroamphenical or tetracycline.

Relative to vectors described previously, the vectors of this invention may be used to obtain enhanced expression of a wide variety of genes encoding desirable polypeptide products. Suitable genes include those encoding growth hormones, e.g., bovine, porcine, chicken or human growth hormones; superoxide dismutase; apolipoprotein E or analogs of any of the preceding. By analog is meant a polypeptide having the same activity as the naturally occurring polypeptide but having one or more different amino acids added or deleted, or both, at the N-terminus of the polypeptide.

The vector may be formed by methods well known to those of ordinary skill in the art to which the invention relates. Such methods are described in greater detail in various publications identified herein, the contents of which are hereby incorporated by reference into the present disclosure in order to provide complete information concerning the state of the art.

One presently preferred vector is the vector p579 with a DNA sequence containing the cI[434] fragment cloned into the ClaI site. p579 has the restriction map shown in FIG. 19.

Plasmids which express an analog of bovine growth hormone having the amino acid sequence met-asp-gln added to the amino terminus of the phenylalanine form of natural bovine growth hormone, have been constructed. One such plasmid is pHG50 which has a restriction map shown in FIG. 6. This plasmid has been deposited in strain A1645 (λi434cI⁻mini Tn10) with the American Type Culture Collection under ATCC No. 37805.

Another such plasmid is pSAL-210/4 which has the restriction map shown in FIG. 9.

Using the same approach other plasmids may be prepared by inserting into the second restriction enzyme site of a vector according to the invention a gene encoding a desired polypeptide.

Various host vector systems involving *Escherichia coli* A1645 and the plasmid described herein may be used to produce different polypeptides such as bovine, porcine, chicken and human growth hormones, human superoxide dismutase and human apolipoprotein E. To do so, the host vector system is grown under suitable conditions permitting production of polypeptide which is then recovered.

Suitable conditions involve growth of the host vector system for an appropriate period of time at about 42° C. Desirably, the period of growth at 42° C is about 1 to 5 hours. Suitable media include casein hydrolysate.

Veterinary compositions may be prepared which contain effective amounts of bGH, analog and a suitable carrier. Such carriers are well known to those of ordinary skill in the art. The analogs may be administered directly or in the form of a composition to a cow in order to increase milk or meat production.

EXAMPLES

The examples which follow are set forth to aid in understanding the invention but are not intended to, and should not be construed to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well known to those of ordinary skill in the art and are described in numerous publications including by way of example the following:

J. Miller, *Experiments in Molecular Genetics*, Cold Spring Harbor Laboratory, New York (1982).

T. Maniatis, E. F. Fritsch and J. Sambrook, *Molecular Cloning; A Laboratory Manual*, Cold Spring Harbor Laboratory, New York (1982).

*Methods in Enzymology*, vol. 65, "Nucleic Acids (Part 1)," edited by Lawrence Grossman and Kivie Moldave, Academic Press, New York (1980).

*Methods in Enzymology*, vol. 68, "Recombinant DNA," edited by Ray Wu, Academic Press, New York (1981).

*Methods in Enzymology*, vol. 100, "Recombinant DNA (Part B)," edited by Ray Wu, Lawrence Grossman and Kivie Moldave, Academic Press, New York (1983).

*Methods in Enzymology*, vol. 101, "Recombinant DNA (Part C)," edited by Ray Wu, Lawrence Grossman and Kivie Moldave, Academic Press, New York (1983).

*Principles of Gene Manipulation, An Introduction to Genetic Engineering*, 2nd Edition, edited by R. W. Old and S. B. Primrose, University of California Press (1981).

H. V. Bernard, et al., Gene (1979) 5, 59.

A. B. Oppenheim, et al., J. Mol. Biol. (1982) 158, 327.

E. Remaut, et al., Gene (1981) 15, 81.

EXAMPLE 1

Bovine Growth Hormone pHG50

The construction of pHG50 is shown in FIG. 6 and is described in the Description of the Figures. The plasmid pHG50 was obtained by insertion of the HpaII-HpaII $\lambda cI^{434}$ fragment of pSK434 (ATCC No. 39784) into the unique ClaI site of pHG44 (ATCC No. 39806). The plasmid pHG51 was constructed in the same way. However, the $\lambda imm434\ cI^+$ fragment is found in the opposite orientation in the plasmid, as compared to plasmid pHG50.

pSK434 (ATCC No. 39784) was constructed by digesting $\lambda imm434$ with BamHI and ligating the mixture to BamHI-digested pBR322. The ligated mixture was transformed into *Escherichia coli* A2097 and colonies immune to $\lambda imm434cI^{3003}$ phage were isolated. The plasmid pSK434 isolated from one of these colonies, contains a 6 kb BamHI fragment which contains the $\lambda cI^{434}$ gene and extends from beyond the N gene to beyond the P gene. pSK434 has the restriction map shown in FIG. 6.

pHG50 and pHG51 were introduced into *Escherichia coli* A1645 by transformation using methods known to those skilled in the art. Clones obtained, designated A3108 and A3112 respectively, produce upon growth and induction an analog of bGH having the amino acid sequence met-asp-gln added to the amino-terminus of the phenylalanine form of natural bGH. The amount of bGH analog produced was in the range of 37-42% of the total protein produced by the bacteria as calculated by scanning Coomasie-stained SDS polyacrylamide gels (Table I).

Prophage Introduction

In order to use the $\lambda cI^{434}$ selection system, the cells containing pHG50 must also contain prophage $\lambda imm434cI^-$. We have used as a prophage $\lambda imm434\ cI^{3003}$ mini Tn10Δ16Δ17. The mini Tn10Δ16Δ17 tetracycline resistance marker (Foster, et al., Cell (1981) 23, 201-213) was introduced into the phage in order to facilitate isolation of rare and stable prophage insertion events. It also permits a simple testing the presence of prophage by monitoring tetracycline resistance.

*Escherichia coli* strain A1645 containing the plasmid pHG50, grown in the presence of ampicillin, was infected at a low multiplicity of infection with $\lambda imm434\ cI^{3003}$ mini Tn10Δ16 Δ17 at 30° C. Tetracycline resistant colonies were isolated and purified. This strain was deposited with the American Type Collection Center under ATCC No. 39805.

In an alternative method, the prophage was introduced by transforming *Escherichia coli* 1645 simultaneously with pHG50 and $\lambda imm434\ cI^{3003}$ mini Tn10Δ16Δ17 and selecting for colonies which are both ampicillin and tetracycline resistant. Suitable hosts for the described vectors and plasmids are strains of *Escherichia coli* suitable for transformation, including A1637, A2602, A1563, A1645 (C600 ΔH ΔBamHI $r^{31}\ m^{30}$ gal+thr-leu-B1) or A2097 (A1645 lac ΔχA21, proC::Tn10). The desired prophage can be introduced into all of the strains in the same manner as described above.

pHG50 and the vector which can be derived from it by excision of the bGH gene, have numerous advantages over previously described expression vectors including:

1. improved plasmid stability

The plasmid contains the $cI^{434}$ repressor gene which represses a $\lambda imm434ci^-$lysogen. Loss of the plasmid results in bacterial cell lysis due to $\lambda imm434cI^-$prophage induction. Thus the plasmid is stably maintained without resort to antibiotic selection schemes which are expensive. Table II demonstrates the increased stability of plasmids carrying $cI^{434}$ stabilization system.

The $cI^{434}$ plasmid stabilization system is compatible with the thermoinducible $\lambda P_L$ promoter expression system, this despite the fact that the thermolabile repressor for the λP$_L$ promoter is C$_I$.

It should be noted that any λimm434cI$^-$prophage can be substituted for the λimm434cI$^{3003}$ prophage. Further, any antibiotic resistance marker can substitute for the tetracycline resistance marker which we introduced on mini Tn10Δ16≠17. The availability of λimm21 and λimm22 repressor negative mutants, allows the replacement of the λ434 system with a comparable system of phage 21 or phage 22.

2. extremely high levels of expression

This plasmid is capable of directing expression of foreign proteins in *Escherichia coli* at levels as high as 42% of the total cellular protein. This level of expression is higher than that described for other similar λP$_L$ plasmids lacking the T$_1$T$_2$ transcription termination sequence.

3. transcription termination signals

The plasmid contains the T$_1$T$_2$ transcription termination signals placed "downstream" from the λP$_L$ promoter and C$_{II}$ ribosomal binding site. The high levels of expression which are obtained when using this plasmid, may be in part to the presence of the T$_1$T$_2$ transcription terminators at the end of the inserted gene, as the T$_1$T$_2$ transcription terminators are capable of terminating transcription of N modified RNA polymerase. Thus the transcription terminators prevent the λP$_L$ controlled transcription of undesired plasmid proteins, thereby enhancing the relative yields of the desired protein.

4. replaceable ribosomal binding site pHG50 contains a unique EcoRI site which is located "upstream" of the ribosomal binding site, and an NdeI site located at the ATG initiation codon. Thus, the ribosomal binding site is bounded by two unique restriction sites. This enables facile excision of the present ribosomal binding site (the λC$_{II}$ ribosomal binding site) and substitution of virtually any other natural or synthetic ribosomal binding site without altering other features of the plasmid. This greatly facilitates optimal expression of desired polypeptides.

5. thermoinducible regulation of expression

The λP$_L$ promoter is inactive when the C$_I$ repressor is bound to it. The cI$^{857}$ repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:

(a) A foreign protein which is toxic to *Escherichia coli* can be produced late thus avoiding early cell death in the fermentation process.

(b) Overproduction of a protein may stabilize the protein and prevent proteolytic degradation. (Cheng, Y.E., et al., Gene (1981) 14, 121). Thus, "instantaneous" overproduction using a tightly regulated promoter such as λP$_L$ may be preferable to continuous low level production.

6. simplified induction protocol pHG50 is induced at about 42° C. and maintained at 42° C. throughout the period of protein synthesis. The induction protocol for plasmids derived from pMG100 and pND5 described in copending, coassigned U.S. patent application Ser. No. 514,188 involved induction at 42° C. followed by an extended period of growth at 38° C. The optimal induction protocol for pHG50 does not require the cooling step to 38° C. and is therefore simplified.

7. high copy number

The λP$_L$ promoter in pHG50 is found on a plasmid with a copy number higher than the λ transducing phage vectors which are present in *Escherichia coli*. This increases expression levels.

8. ribosome binding site and initiation codon. This expression vector contains a strong procaryotic ribosomal binding site (RBS) as well as a translation initiation codon (ATG). Thus, any eucaryotic gene may be cloned without adding an initiation codon. Furthermore, the efficient RBS increases levels of expression. The ribosome binding site is the λC$_{II}$ ribosomal binding site. The sequence of the ribosomal binding site is:

TAAGGAAGTACTTACAT

ATTCCTTCATGAATGTA

One base pair is different from the ribosomal binding site found in the wild type λ.

9. convenient restriction site

The expression vector derived from the plasmid has a unique NdeI restriction site which contains within the site the ATG initiation codon. This permits proper positioning of the desired gene. The unique NdeI site is found immediately after the ribosomal binding site.

10. nut site

N protein, which is provided by the host, binds the Nut site on the expression vector and thereby prevents termination of transcription at the t$_{RI}$ site or premature transcription termination within the cloned gene.

TABLE I[1]

| Plasmid | % bGH[2] | Remarks |
| --- | --- | --- |
| pRec 2/3 | 23 | Amp$^R$ |
| pRO11 | 28 | Amp$^R$ |
| pRO12 | 30–36 | Amp$^R$ |
| pHG44 | 37–42 | Amp$^R$,T$_1$T$_2$ |
| pHG50 | 37–42 | Amp$^R$,T$_1$T$_2$;cI$^{434}$ |
| pSAL-130/5 | 39–44 | Amp$^R$;CHCN;T$_1$T$_2$ |
| pSAL-170/10 | 40–46 | Tet$^R$;CHCN;T$_1$T$_2$ |

1. The table lists the expression levels of bGH analog attained with pHG50 and other λP$_L$ plasmids. pRec2/3 and pRO11 are described in copending, coassigned U.S. patent application Ser. No. 514,188, filed July 15, 1983.
2. Amount of bGH produced as percentage of total bacterial protein.

ABBREVIATIONS

CHCN = Constitutive high copy number
Amp$^R$ = Ampicillin resistance
Tet$^R$ = Tetracycline resistance
T$_1$T$_2$ = Transcription termination sequences
cI$^{434}$ = Plasmid stabilization cI$^{434}$ system

TABLE II

Plasmid Stabilization Resulting from the cI$^{434}$ System

| Strain | Plasmid | Host | % of Cells Without Plasmid |
| --- | --- | --- | --- |
| A3102 | pHG44 | A2097 | 10–20 |
| A3108 | pHG50 | A1645 | 10–20 |
| A3109 | pHG50 | A1645 (λi434cI$^-$ mini Tn10) | <1.0 |
| A3112 | pHG51 | A1645 | 10–20 |
| A3113 | pHG51 | A1645 | <1.0 |

TABLE II-continued

Plasmid Stabilization Resulting from the cI$^{434}$ System

| Strain | Plasmid | Host | % of Cells Without Plasmid |
|--------|---------|------|----------------------------|
| | | ($\lambda$i434cI$^-$ mini Tn10) | |

Strains A3108 and A3112 were infected with $\lambda$imm434I$^-$mini Tn10 at 30° C. and tetracycline resistant colonies were isolated. The colonies were purified and tested for ampicillin resistance. Single colonies were selected and grown overnight at 30° C. in LB medium containing 50 μg/ml ampicillin. The cultures were diluted 1/1000 into LB medium, grown to about $5 \times 10^8$/ml, and further diluted 1/100,000 into fresh LB and grown overnight. Samples were spread on LB plates and on LB plates containing 50 μg/ml ampicillin. About 50 colonies from each LB plate were checked for growth on LB plates containing ampicillin. The results demonstrate plasmid stability of selected clones.

EXAMPLE 2

Growth of pHG50

I. Stock Cultures

Stock cultures of pHG50 were grown on casein medium (see Inoculum), then diluted two-fold with freezing medium and stored at −80° C. Freezing medium contains per 500 ml:

| K$_2$HPO$_4$ | 6.3 g |
|---|---|
| KH$_2$PO$_4$ | 1.8 g |
| Na Citrate | 0.45 g |
| MgSO$_4$.7H$_2$O | 0.09 g |
| (NH$_4$)$_2$SO$_4$ | 0.9 g |
| Glycerol | 44.0 g |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C and approximately 200 r.p.m. As needed subsequent stages in inoculum propagation were carried out in stirred aerated fermenters. Sterile medium was inoculated with 2-10% inoculum and incubated 15 hours at 30° C., pH 7±0.5 with agitation and aeration to maintain a dissolved oxygen level above 20% air saturation.

III. Production

The production medium contains:

| Casein hydrolysate | 20 g/l |
|---|---|
| Yeast extract | 10 g/l |
| K$_2$HPO$_4$ | 2.5 g/l |
| MgSO$_4$.7H$_2$O | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine and ampicillin in concentrated solution were filter sterilized separately and added to the sterile production medium before inoculation. Sterile glucose solution was added initially to supply 10 g/l. At the induction step another 10 g/l of glucose was added.

The trace elements solution contains

| FeCl$_3$ | 16 g/l |
|---|---|
| ZnCl$_2$.4H$_2$O | 2 g/l |
| CoCl$_2$.6H$_2$O | 2 g/l |
| Na$_2$MoO$_4$.2H$_2$O | 2 g/l |
| CaCl$_2$.2H$_2$O | 1 g/l |
| CuCl$_2$ | 1 g/l |
| H$_3$BO$_3$ | 0.5 g/l |
| Conc. HCl | 100 ml/l |

The medium is inoculated with 0.5-10% inoculum culture and incubated at 30° C. Agitation-aeration rate are set to maintain a dissolved oxygen level above 20% air saturation. The pH is maintained at 7±0.2 with NH$_3$. Once cell concentration reaches about 3.5 g/l (OD$_{660}$=10) induction is started.

The temperature is raised to 42° C. and maintained at 42° C. for 1-5 hours. The culture is then chilled and cells are recovered by centrifugation for hormone purification.

What is claimed is:

1. The plasmid designated pHG50 which has been deposited under ATCC Accession No. 39805.

2. A host plasmid system for production of a polypeptide analog of bovine growth hormone comprising the plasmid of claim 1 in a suitable *Escherichia coli* host.

3. The host plasmid system of claim 2, wherein the host is *Escherichia coli* A1645 ($\lambda$i434cI$^-$mini Tn10).

4. A method for producing a polypeptide analog of bovine growth hormone which comprises growing the host plasmid system of claim 2 and 3 under suitable conditions permitting production of the polypeptide analog of bovine growth hormone and recovering the resulting polypeptide analog of bovine growth hormone.

* * * * *